(12) United States Patent
Ehninger

(10) Patent No.: US 11,560,426 B2
(45) Date of Patent: Jan. 24, 2023

(54) TARGETING MODULES FOR UNIVERSAL CHIMERIC ANTIGEN RECEPTOR EXPRESSING IMMUNE CELLS AND USE IN THE TREATMENT OF CANCER INFECTIONS AND AUTOIMMUNE DISORDERS

(71) Applicant: AvenCell Europe GmbH, Dresden (DE)

(72) Inventor: Armin Ehninger, Dresden (DE)

(73) Assignee: AvenCell Europe GmbH, Dresden (DE)

( * ) Notice: Subject to any disclaimer, the term of this patent is extended or adjusted under 35 U.S.C. 154(b) by 153 days.

(21) Appl. No.: 16/618,881

(22) PCT Filed: Jun. 8, 2018

(86) PCT No.: PCT/EP2018/065193
§ 371 (c)(1),
(2) Date: Dec. 3, 2019

(87) PCT Pub. No.: WO2018/224660
PCT Pub. Date: Dec. 13, 2018

(65) Prior Publication Data
US 2020/0131262 A1 Apr. 30, 2020

(30) Foreign Application Priority Data
Jun. 9, 2017 (EP) ..................................... 17175124

(51) Int. Cl.
*C07K 16/28* (2006.01)
*C07K 14/55* (2006.01)
*C07K 14/725* (2006.01)
*C07K 14/705* (2006.01)
*A61K 38/10* (2006.01)
*A61K 38/31* (2006.01)
*A61K 38/22* (2006.01)
*A61K 38/26* (2006.01)
*A61K 47/62* (2017.01)
*A61K 38/18* (2006.01)
*A61K 38/00* (2006.01)

(52) U.S. Cl.
CPC ............ *C07K 16/28* (2013.01); *A61K 38/105* (2013.01); *A61K 38/1883* (2013.01); *A61K 38/2207* (2013.01); *A61K 38/2278* (2013.01); *A61K 38/26* (2013.01); *A61K 38/31* (2013.01); *A61K 47/62* (2017.08); *C07K 14/55* (2013.01); *C07K 14/7051* (2013.01); *C07K 14/70521* (2013.01); *C07K 14/70578* (2013.01); *A61K 38/00* (2013.01); *C07K 2317/24* (2013.01); *C07K 2317/53* (2013.01); *C07K 2317/622* (2013.01); *C07K 2319/02* (2013.01); *C07K 2319/03* (2013.01); *C07K 2319/30* (2013.01); *C07K 2319/33* (2013.01)

(58) Field of Classification Search
None
See application file for complete search history.

(56) References Cited

FOREIGN PATENT DOCUMENTS

| EP | 2990416 A1 | 3/2016 |
| WO | 2010/108125 A2 | 9/2010 |
| WO | 2012/082841 A2 | 6/2012 |
| WO | 2013/044225 A1 | 3/2013 |
| WO | 2015/055318 A1 | 4/2015 |
| WO | WO-2016030414 A1 * | 3/2016 ............ A61K 35/17 |

OTHER PUBLICATIONS

Jiménez-Mancilla et al. ("Multifunctional targeted therapy system based on 99mTc/177Lu-labeled gold nanoparticles-Tat(49-57)-Lys3-bombesin internalized in nuclei of prostate cancer cells," J. Label Compd. Radiopharm 2013, 56 663-671 (Year: 2013).*
Liolios et al. "Novel Bispecific PSMA/GRPr Targeting Radioligands with Optimized Pharmacokinetics for Improved PET Imaging of Prostate Cancer," Bioconjugate Chem. 2016, 27, 737-751, published Jan. 4, 2016 (Year: 2016).*
Results for NCBI BLAST search for peptide sequence HEHEHE conducted Feb. 11, 2022 (Year: 2022).*
International Search Report and Written Opinion of the International Searching Authority for International Application No. PCT/EP2018/065193 dated Sep. 17, 2018.
Afshar-Oromieh, A., et al., "The Theranostic PSMA Ligand PSMA-617 in the Diagnosis of Prostate Cancer by PET/CT: Biodistribution in Humans, Radiation Dosimetry, and First Evaluation of Tumor Lesions", The Journal of Nuclear Medicine, vol. 56, No. 11, pp. 1697-1705 (2015).
Arap, W., et al., "Cancer Treatment by Targeted Drug Delivery to Tumor Vasculature in a Mouse Model", Science, vol. 279, pp. 377-380 (1998).
Arap, M.A., et al., "Cell surface expression of the stress response chaperone GRP78 enables tumor targeting by circulating ligands", Cancer Cell, vol. 6, pp. 275-284 (2004).
Barrett, J.A., et al., "First-in-Man Evaluation of 2 High-Affinity PSMA-Avid Small Molecules for Imaging Prostate Cancer", The Journal of Nuclear Medicine, vol. 54, No. 3, pp. 380-387 (2013).
Beaujouan, J.-C., et al., "A 25 year adventure in the fields of tachykinins", Peptides, vol. 25, pp. 339-357 (2004).
Brady, L.W., et al., "Therapeutic Nuclear Medicine", Springer. DOI 10.1007/978-3-540-36719-2., pp. 1-951 (2014).

(Continued)

Primary Examiner — Christina Bradley
(74) Attorney, Agent, or Firm — Choate, Hall & Stewart LLP; Charles E. Lyon

(57) ABSTRACT

The present invention relates to a targeting module comprising a chemically synthesized peptide binding moiety specific for a human cell surface protein or protein complex, a kit comprising the targeting module and a vector or a cell comprising a nucleic acid encoding a universal chimeric antigen receptor and the use for the treatment of cancer, infections and autoimmune disorders.

12 Claims, 6 Drawing Sheets
Specification includes a Sequence Listing.

(56) References Cited

OTHER PUBLICATIONS

Broda, E., et al., "Assessing potential peptide targeting ligands by quantification of cellular adhesion of model nanoparticles under flow conditions", Journal of Controlled Release, vol. 213, pp. 79-85 (2015).
Brom, M., et al., "$^{68}$Ga-labelled exendin-3, a new agent for the detection of insulinomas with PET", European Journal of Nuclear Medicine and Molecular Imaging, vol. 37, pp. 1345-1355 (2010).
Buchegger, F., et al., "Radiolabeled Neurotensin Analog, $^{99m}$Tc-NT-XI, Evaluated in Ductal Pancreatic Adenocarcinoma Patients", Neurotensin Receptor Targeting, vol. 44, No. 10, pp. 1649-1654 (2003).
Burg, M.A., et al., "NG2 Proteoglycan-binding Peptides Target Tumor Neovasculature", Cancer Research, vol. 59, pp. 2869-2874 (1999).
Cardó-Vila, M., et al., "αvβ5 Integrin-Dependent Programmed Cell Death Triggered by a Peptide Mimic of Annexin V", Molecular Cell, vol. 11, pp. 1151-1162 (2003).
Cardó-Vila, M., et al., "A Ligand Peptide Motif Selected from a Cancer Patient Is a Receptor-Interacting Site within Human Interleukin-11", PLOS ONE, vol. 3, Issue 10, pp. e345, 1-11 (2008).
Cardó-Vila, M., et al., "From combinatorial peptide selection to drug prototype (II): Targeting the epidermal growth factor receptor pathway", PNAS, vol. 107, No. 11, pp. 5118-5123 (2010).
Carpenito, C., et al., "Control of large, established tumor xenografts with genetically retargeted human T cells containing CD28 and CD137 domains", PNAS, vol. 106, No. 9, pp. 3360-3365 (2009).
Cartellieri, M., et al., "A Novel Ex Vivo Isolation and Expansion Procedure for Chimeric Antigen Receptor Engrafted Human T Cells", PLOS ONE, vol. 9, Issue 4, pp. e93745, 1-12 (2014).
Cartellieri, M., et al., "Switching Car T cells on and off: a novel modular platform for retargeting of T cells to AML blasts", Blood Cancer Journal, vol. 6, pp. e458, 1-8 (2016).
Chen, J., et al., "α-Melanocyte-Stimulating Hormone Peptide Analogs Labeled with Technetium-99m and Indium-111 for Malignant Melanoma Targeting", Cancer, vol. 94, No. 4, pp. 196-1201 (2002).
Clark-Lewis, I., et al., "Structure-Activity Relationships of Interleukin-8 Determined Using Chemically Synthesized Analogs", The Journal of Biological Chemistry, vol. 266, No. 34, pp. 23128-23134 (1991).
De Rosa, L., et al., "Miniaturizing VEGF: Peptides mimicking the discontinuous VEGF receptor-binding site modulate the angiogenie response", Scientific Reports, pp. 1-13 (2016).
De Visser, M., et al., "Stabilised $^{111}$In-labelled DTPA- and DOTA-conjugated neurotensin analogues for imaging and therapy of exocrine pancreatic cancer", European Journal of Nuclear Medicine and Molecular Imaging, vol. 30, pp. 1134-1139 (2003).
Decristoforo, C., et al., "$^{68}$Ga- and $^{111}$In-labelled DOTA-RGD peptides for imaging of αvβ3 integrin expression", European Journal of Nuclear Medicine and Molecular Imaging, vol. 35, pp. 1507-1515 (2008).
Dumont, R.A., et al., "Novel $^{64}$Cu- and $^{68}$Ga-Labeled RGD Conjugates Show Improved PET Imaging of $\alpha_v\beta_3$ Integrin Expression and Facile Radiosythesis", The Journal of Nuclear Medicine, vol. 52, No. 8, pp. 1276-1284 (2011).
Federov, V.D., et al., "PD-1- and CTLA-4-Based Inhibitory Chimeric Antigen Receptors (iCARs) Divert Off-Target Immunotherapy Responses", Sci Transl Med., vol. 11, No. 215, 215ra172.
Finney, H.M., et al., "Activation of Resting Human Primary T Cells with Chimeric Receptors: Costimulation from CD28, Inducible Costimulator, CD134, and CD137 in Series with Signals from the TCRζ Chain", The Journal of Immunology, vol. 172, pp. 104-113 (2004).
Frigault, M.J., et al., "Identification of chimeric antigen receptors that mediate constitutive or inducible proliferation of T cells", Cancer Immunol Res., vol. 3, No. 4, pp. 356-367 (2015).
Fröberg, A.C., et al., "Comparison of three radiolabeled peptide analogues for CCK-2 receptor scintigraphy in medullary thyroid carcinoma", European Journal of Nuclear Medicine and Molecular Imaging, vol. 36, pp. 1265-1272 (2009).
Gade, T.P.F., et al., "Targeted Elimination of Prostate Cancer by Genetically Directed Human T Lymphocytes", Cancer Research, vol. 65, No. 19, pp. 9080-9088 (2005).
Gong, M.C., et al., "Cancer Patient T Cells Genetically Targeted to Prostate-Specific Membrane Antigen Specifically Lyse Prostate Cancer Cells and Release Cytokines in Response to Prostate-Specific Membrane Antigen", Neoplasia, vol. 1, No. 2, pp. 123-127 (1999).
Gonzalez, N. et al., "Bombesin-Related Peptides and their receptors: recent advances in their role in physiology and disease states", Curr Opin Endocrinol Diabetes Obes., vol. 15, No. 1, pp. 58-64 (2008).
Grupp, S.A., et al., "Chimeric Antigen Receptor—Modified T Cells for Acute Lymphoid Leukemia", The New England Journal of Medicine, vol. 368, No. 16, pp. 1509-1518 (2013).
Hanaoka, H., et al., "Development of a $^{111}$In-labeled peptide derivative targeting a chemokine receptor, CXCR4, for imaging tumors", Nuclear Medicine and Biology, vol. 33, pp. 489-494 (2006).
Haubner, R., et al., "Noninvasive Visualization of the Activated αvβ3 Integrin in Cancer Patients by Positron Emission Tomography and [$^{18}$F]Galacto-RGD", PLoS Medicine, vol. 2, Issue 3, pp. e70, 0244-0252 (2005).
Hessenius, C., et al., "Vasoactive intestinal peptide receptor scintigraphy in patients with pancreatic adenocarcinomas or neuroendocrine tumours", European Journal of Nuclear Medicine, vol. 27, No. 11, pp. 1684-1693 (2000).
Hombach, A., et al., "T-Cell Activation by Recombinant Receptors: CD28 Costimulation Is Required for Interleukin 2 Secretion and Receptor-mediated T-Cell Proliferation but Does Not Affect Receptor-mediated Target Cell Lysis", vol. 61, pp. 1976-1982 (2001).
Hombach, A.A., et al., "Effective Proliferation of Human Regulatory T Cells Requires a Strong Costimulatory CD28 Signal That Cannot Be Substituted by IL-2", The Journal of Immunology, vol. 179, pp. 7924-7931 (2007).
Hombach, A.A., et al., "Of chimeric antigen receptors and antibodies: OX40 and 41BB costimulation sharpen up T cell-based immunotherapy of cancer", Immunotherapy, vol. 5, No. 7, pp. 677-681 (2013).
Iwasaki, K., et al., "A Fluorescent Imaging Probe Based on a Macrocyclic Scaffold That Binds to Cellular EpCAM", J Mol Evol, vol. 81, pp. 210-217 (2015).
Jacobson, O., et al., "PET of Tumor CXCR4 Expression with 4-$^{18}$F-T140", The Journal of Nuclear Medicine, vol. 51, No. 11, pp. 1796-1804 (2010).
Kajiwara, K., et al., "Synthetic peptides, corresponding to ligand-binding region of death receptors, DR5, Fas, and TNFR, specifically inhibit cell death mediated by the death ligands, respectively", Biochimica et Biophysica Acta, vol. 1699, pp. 131-137 (2004).
Kaltsas, G.A., et al., "Treatment of advanced neuroendocrine tumours with radiolabeled somatostatin analogues", Endocrine-Related Cancer, vol. 12, pp. 683-699 (2005).
Karjalainen, K., et al., "Targeting neuropilin-1 in human leukemia and lymphoma", Blood, vol. 117, No. 3, pp. 920-927 (2011).
Kershaw, M.H., et al., "A Phase I Study on Adoptive Immunotherapy Using Gene-Modified T Cells for Ovarian Cancer", vol. 12, No. 20 Pt 1, pp. 6106-6115 (2006).
Kolenc-Peitl, P., et al., "Highly Improved Metabolic Stability and Pharmacokinetics of Indium-111-DOTA-Gastrin Conjugates for Targeting of the Gastrin Receptor", Journal of Medicinal Chemistry, vol. 54, pp. 2602-2609 (2011).
Kolonin, M.G., et al., "Ligand-Directed Surface Profiling of Human Cancer Cells with Combinatorial Peptide Libraries", Cancer Research, vol. 66, No. 1, pp. 34-40 (2006).
Lamers, C.H., et al., "Adoptive immune-gene therapy of cancer with single chain antibody [scFv(Ig)] gene modified T lymphocytes.", J Biol Regul Homeost Agents, vol. 18, No. 2, pp. 134-140 (2004) Abstract Only.
Lamers, C.H.J., et al., "Treatment of Metastatic Renal Cell Carcinoma With Autologous T-Lymphocytes Genetically Retargeted Against Carbonic Anhydrase IX: First Clinical Experience", Journal of Clinical Oncology, vol. 24, No. 13, pp. e20-e22 (2006).

(56) References Cited

OTHER PUBLICATIONS

Laverman, P., et al., "Radiolabelled peptides for oncological diagnosis", European Journal of Nuclear Medicine and Molecular Imaging, vol. 39, Suppl 1, pp. S78-S92 (2012).
Maher, J., et al., "Human T-lymphocyte cytotoxicity and proliferation directed by a single chimeric. TCRζ/CD28 receptor", Nature Biotechnology, vol. 20, pp. 70-75 (2002).
Marchiò, S., et al., "Aminopeptidase A is a functional target in angiogenic blood vessels", Cancer Cell, vol. 5, pp. 151-162 (2004).
Merlo, A., et al., "Locoregional Regulatory Peptide Receptor Targeting with the Diffusible Somatostatin Analogue $^{90}$Y-Labeled DOTA$^{0}$-$_{D}$-Phe$^{1}$-Tyr$^{3}$-octreotide (DOTATOC): A Pilot Study in Human Gliomas", Clinical Cancer Research, vol. 5, pp. 1025-1033 (1999).
Michaloski, J.S., et al., "Discovery of pan-VEGF inhibitory peptides directed to the extracellular ligand-binding domains of the VEGF receptors", Science Advances, vol. 2, pp. e1600611, 1-13 (2016).
Milone, M.C., et al., "Chimeric Receptors Containing CD137 Signal Transduction Domains Mediate Enhanced Survival of T Cells and Increased Antileukemic Efficacy in Vivo", Molecular Therapy, vol. 17, No. 8, pp. 1453-1464 (2009).
Morgan, R.A., et al., "Case Report of a Serious Adverse Event Following the Administration of T Cells Transduced With a Chimeric Antigen Receptor Recognizing ERBB2", Molecular Therapy, vol. 18, No. 4, pp. 843-851 (2010).
Nagy, A., et al., "Targeting of Cytotoxic Luteininzing Hormone-Releasing Hormone Analogs to Breast, Ovarian, Endometrial, and Prostate Cancers", Biology of Reproduction, vol. 73, pp. 851-859 (2005).
Ohki-Hamazaki, H. et al., "Development and function of bombesin-like peptides and their receptors", Int. J. Dev. Biol., vol. 49, pp. 293-300 (2005).
Pasqualini, R., et al., "Aminopeptidase N Is a Receptor for Tumor-homing Peptides and a Target for Inhibiting Angiogenesis", Cancer Research, vol. 60, No. 3, pp. 722-727 (2000).
Pinthus, J.H., et al., "Immuno-Gene Therapy of Established Prostate Tumors Using Chimeric Receptor-redirected Human Lymphocytes", Cancer Research, vol. 63, pp. 2470-2476 (2003).
Pinthus, J.H., et al., "Adoptive immunotherapy of prostate cancer bone lesions using redirected effector lymphocytes", The Journal of Clinical Investigation, vol. 114, No. 12, pp. 1774-1781 (2004).
Popovics, P., et al., "Targeted cytotoxic analogs of luteinizing hormone-releasing hormone (LHRH), AEZS0108 (AN-152), inhibits the growth of DU-145 human castration-resistant prostate cancer in vivo and in vitro through elevating p21 and ROS levels," Oncotarget, vol. 5, No. 12, pp. 4567-4578 (2014).
Raderer, M., et al., "Value of Peptide Receptor Scintigraphy Using $^{123}$I-Vasoactive Intestinal Peptide and $^{111}$In-DTPA-D-Phe$^{1}$-Octreotide in 194 Carcinoid Patients: Vienna University Experience, 1993 to 1998", J Clin Oncol, vol. 18, pp. 1331-1336 (2000).
Reubi, J.C., et al., "Y$_{1}$-Mediated Effect of Neuropeptide Y in Cancer: Breast Carcinomas as Targets", Cancer Research, vol. 61, pp. 4636-4641 (2001).
Sai, K.K.S., et al., "Peptide-based PET imaging of the tumor restricted IL13RA2 biomarker", Octotarget, vol. 8, No. 31, pp. 50997-51007 (2017).
Soudy, R., et al., "Breast Cancer Targeting Peptide Binds Keratin 1: A New Molecular Marker for Targeted Drug Delivery to Breast Cancer", Molecular Pharmaceuticals, vol. 14, pp. 593-604 (2017).
Staquicini, F.I., et al., "Receptor Tyrosine Kinase EphA5 Is a Functional Molecular Target in Human Lung Cancer", The Journal of Biological Chemistry, vol. 290, No. 12, pp. 7345-7359 (2015).

Staquicini, F.I., et al., "A Subset of Host B-Lymphocytes Control Melanoma Metastasis Through a MCAM/MUC18-dependent Interaction: Evidence from Mice and Humans", Cancer Research, vol. 68, No. 20, pp. 8419-8428 (2008).
Töpfer, K., et al., DAP12-Based Activating Chimeric Antigen Receptor for NK Cell Tumor Immunotherapy, The Journal of Immunology, vol. 194, pp. 3201-3212 (2015).
Vallabhajosula, S., et al., "$^{99m}$Tc-Labeled Small-Molecule Inhibitors of Prostate-Specific Membrane Antigen: Pharmacokinetics and Biodistribution Studies in Healthy Subjects and Patients with Metastatic Prostate Cancer", The Journal of Nuclear Medicine, vol. 55, pp. 1791-1798 (2014).
Vidal, C.I., et al., "An HSP90-mimic peptide revealed by fingerprinting the pool of antibodies from ovarian cancer patients", Oncogene, vol. 23, pp. 8859-8867 (2004).
Wang, X.-F., et al., "A Peptide Conjugate of Vitamin E Succinate Targets Breast Cancer Cells with High ErbB2 Expression", Cancer Research, vol. 67, No. 7, pp. 3337-3344 (2007).
Wang, J., et al., "Optimizing Adoptive Polyclonal T Cell Immunotherapy of Lymphomas, Using a Chimeric T Cell Receptor Possessing CD28 and CD137 Costimulatory Domains", Human Gene Therapy, vol. 18, pp. 712-725 (2007).
Wild, D., et al., "[Lys$^{40}$(Ahx-DTPA-$^{111}$In)NH$_{2}$]Exendin-4, a Very Promising Ligand for Glucagon-like Peptide-1 (GLP-1) Receptor Targeting", The Journal of Nuclear Medicine, vol. 47, pp. 2025-2033 (2006).
Wild, D., et al., "Exendin-4-Based Radiopharmaceuticals for Glucagon-like Peptide-1 Receptor PET/CT and SPECT/CT", The Journal of Nuclear Medicine, vol. 51, pp. 1059-1067 (2010).
Wild, D., et al., "First Clinical Evidence That Imaging with Somatostatin Receptor Antagonists is Feasible", The Journal of Nuclear Medicine, vol. 52, pp. 1412-1417 (2011).
Yang, J., et al., "Evaluation of a Novel Arg-Gly-Asp-Conjugated Alpha-Melanocyte Stimulating Hormone Hybrid Peptide for Potential Melanoma Therapy", Bioconjug Chem., vol. 20, No. 8, pp. 1634-1642 (2009).
Zhang, T., et al., "Chimeric NK-receptor-bearing T cells mediate antitumor immunotherapy", Blood, vol. 106, No. 5, pp. 1544-1551 (2005).
Zhang, T., et al., "Generation of Antitumor Responses by Genetic Modification of Primary Human T Cells with a Chimeric NKG2D Receptor", Cancer Research, vol. 66, No. 11, pp. 5927-5933 (2006).
Zhao, Y., et al., "A Herceptin-Based Chimeric Antigen Receptor with Modified Signaling Domains Leads to Enhanced Survival of Transduced T Lymphocytes and Antitumor Activity", The Journal of Immunology, vol. 183, pp. 5563-5574 (2009).
Cartellieri, M., et al., "Unicar: A Novel Modular Retargeting Platform Technology for CAR T Cells", Blood, vol. 126, No. 23, XP002776535, 57$^{th}$ Annual Meeting of Hematology; Orlando, FL, USA, pp. 1-5 (2015).
Eder, M., et al., "Preclinical Evaluation of a Bispecific Low-Molecular Heterodimer Targeting Both PSMA and GRPR for Improved PET Imaging and Therapy of Prostate Cancer", The Prostate, vol. 74, pp. 659-668 (2014).
Giesel, F.L., et al., "PSMA PET/CT with Glu-urea-Lys-(Ahx)-$^{68}$Ga(HBED-CC)] versus 3D Ct volumetric lymph node assessment in recurrent prostate cancer", European Journal of Nuclear Medicine and Molecular Imaging, vol. 42, pp. 1794-1800 (2015).
Krenciute, G., et al., "A scFv-Based CAR to Redirect T Cells to IL13Ra2-Positive Glioma", Molecular Therapy, vol. 23, Supplement 1, p. S113 (2015).

* cited by examiner

TARGETING MODULES FOR UNIVERSAL CHIMERIC ANTIGEN RECEPTOR EXPRESSING IMMUNE CELLS AND USE IN THE TREATMENT OF CANCER INFECTIONS AND AUTOIMMUNE DISORDERS

CROSS REFERENCE TO RELATED APPLICATIONS

This application is a national stage filing under section 371 of International Application No. PCT/EP2018/065193, filed on Jun. 8, 2018, and published on Dec. 13, 2018 as WO 2018/224660, which claims priority to European Application No. 17175124.1, filed on Jun. 9, 2017. The entire contents of WO 2018/224660 are hereby incorporated herein by reference.

SEQUENCE LISTING

The instant application contains a Sequence Listing which has been filed electronically in ASCII format and is hereby incorporated by reference in its entirety. Said ASCII copy, created on Jun. 13, 2022, is named 2013449-0009_SL.txt and is 40,982 bytes in size.

The present invention relates to a targeting module comprising a chemically synthesized peptide binding moiety specific for a human cell surface protein or protein complex, a kit comprising the targeting module and a vector or a cell comprising a nucleic acid encoding a universal chimeric antigen receptor and the use for the treatment of cancer, infections and autoimmune disorders.

Chimeric antigen receptors (CARs) are artificial receptors consisting of a binding moiety, which provides the antigen-specificity and one or several signaling chains derived from immune receptors (Cartellieri et al. 2010). These two principal CAR domains are connected by a linking peptide chain including a transmembrane domain, which anchors the CAR in the cellular plasma membrane. Immune cells, in particular T and NK lymphocytes, can be genetically modified to express CARs inserted into their plasma membrane. If such a CAR modified immune cell encounters other cells or tissue structures expressing or being decorated with the appropriate target of the CAR binding moiety, upon binding of the CAR binding moiety to the target antigen the CAR modified immune cell is cross-linked to the target. Cross-linking leads to an induction of signal pathways via the CAR signaling chains, which will change the biologic properties of the CAR engrafted immune cell. The adoptive transfer of immune cells engineered with chimeric antigen receptors (CARs) is currently considered as a highly promising therapeutic option for treatment of otherwise incurable malignant, infectious or autoimmune diseases. First clinical trials demonstrated both the safety and the feasibility of this treatment strategy (Lamers et al. 2006, Kershaw et al. 2006). However, the conventional CAR technology comes along with a number of critical safety issues. The immune responses of T cells engineered with conventional CARs are difficult to control after infusion into the patient, in particular unexpected target gene expression on healthy tissue may provoke an immune reaction of engineered T cells against healthy cells, which can cause severe side effects (Lamers et al. 2006, Morgan et al. 2010). Another drawback of conventional CAR technology is the restriction of engineered T cell retargeting to a single antigen. Such a monotherapeutic approach implies the risk for development of tumor escape variants, which have lost the target antigen during treatment. The emergence of tumor escape variants under conventional CAR T cell therapy after several months was already observed in clinical trials (Grupp et al. 2013).

WO 2012082841 A2 discloses universal anti-tag chimeric antigen receptor-expressing T cells and methods of treating cell related disorders, e.g. cancer. Furthermore, WO 2013044225 A1 discloses a universal immune receptor expressed by T cells for the targeting of diverse and multiple antigens. Both methods describe the use of modified T cells expressing universal anti-tag immune receptors. These T cells can be redirected to disease-related cell surface antigens by additionally applying modules binding these surface antigens and carrying the respective tag. The disadvantage is the redirection of the genetically modified T cells using exogenous tags, which are likely immunogenic and therefore put patients in danger and negatively affect efficacy of treatment.

Alternatively, EP 2 990 416 A1 discloses a genetically modified immune cell, in particular T- and NK-cell based therapies, that allows a redirection against diverse disorders in a safe and efficient manner using endogenous tags based on nuclear proteins. In particular, EP 2 990 416 A1 discloses a nucleic acid encoding a universal chimeric antigen receptor (UniCAR) and a targeting module composed of a binding moiety specific for a certain human cell surface protein or protein complex and a tag, wherein the tag is derived from any human nuclear protein and their use for stimulating an immune response in mammals. In contrast to conventional CARs, the scFv in universal CARs does not recognize a cell surface antigen but a short nonimmunogenic peptide motif derived from a human nuclear protein. Thus, T cells engineered to express UniCARs remain inactive after reinfusion, as this UniCAR target is not available on the surface of intact cells under physiological conditions (FIG. 1). The targeting modules are based on recombinant proteins including antibody fragments (i.e. scFvs or Fabs), ligands or soluble receptors.

A disadvantage of the disclosed method is the highly complex production and purification procedure, which needs to be established and performed, to obtain clinical-grade targeting modules. This includes recombinant expression in prokaryotic or mammalian cell culture systems, complex multi-step chromatography procedures for purification and extensive analytical panels for quality control. Moreover, the stability of the targeting modules is often limited and long-term storage conditions are disadvantageous.

In a first aspect the invention provides specific targeting modules, which are easily, rapidly and economically manufactured on a clinical-grade level.

Furthermore, the present invention provides specific targeting modules with improved pharmaceutical properties; and improved stability.

Embodiments of the invention relate to a targeting module comprising a chemically synthesized peptide binding moiety specific for a human cell surface protein or protein complex, and a tag, wherein the tag is a peptide derived from any protein, wherein the targeting module is a peptide comprising 10 to 120 amino acids.

In embodiments the linear peptide epitope is derived from a human protein to minimize the risk for immunogenicity.

In further embodiments the linear peptide epitope is derived from a human nuclear protein to minimize the risk for immunogenicity and to prevent off target activity of the UniCAR expressing immune cell. A peptide of a nuclear human protein will not be presented on cell surface and thus, UniCAR engrafted immune cells cannot be activated in the absence of a targeting module (FIG. 1).

Advantageously, the targeting module according to the invention is easily synthesizable. Furthermore advantageously, the targeting module according to the invention is able to bind to a universal chimeric antigen receptor (UniCAR) and to a human cell surface protein or protein complex.

A targeting module according to the invention is a molecule, which enables the genetically modified immune cell to reach its target, in particular a cellular surface protein or an extracellular structure.

As used herein, the term "chemically synthesized" refers to a method of production of peptides by chemical synthesis, in particular by coupling of a carboxyl group of a first amino acid with the amino group of a second amino acid. In an embodiment, the chemical synthesis is selected from liquid-phase synthesis or solid-phase synthesis.

As used herein, the term "specific" refers to the ability of a peptide or a protein to bind exclusively to a target or to a group of targets.

As used herein, the term "cell surface protein or protein complex" refers to a cellular surface protein or an extracellular structure. As used herein, the term "protein complex" refers to a group of two or more associated protein chains.

Brady et al. discloses peptides specific for a human cell surface protein or protein complex and the corresponding receptor types or subtypes overexpressed in human tumor cells (Brady et al. 2014).

As used herein, the term "tag" refers to a peptide sequence attached to peptides or proteins to enable them to bind to specific atoms, ions or molecules.

A human protein according to the invention is a protein found in human organisms.

A nuclear protein according to the invention is a protein found in the cell nucleus.

In further embodiments, the targeting module is chemically synthesized.

According to the invention, the chemically synthesized peptide binding moiety is selected from somatostatin and somatostatin analogues, somatostatin antagonists, bombesin and bombesin analogues, gastrin-releasing peptide (GRP) and GRP analogues, neuromedin B and neuromedin B analogues, vasoactive secretin family, melanocyte-stimulating hormones (MSH) and MSH analogues, cholecystokinins (CCK), gastrins, neurotensin and neurotensin analogues, gonadotropin-releasing hormone family, neurokines, exendins or exenatides, Arg-Gly-Asp (RGD) peptides, Asn-Gly-Arg (NGR) peptides, neuregulins or wherein the chemically synthesized peptide binding moiety has binding specificity to membrane receptors.

As used herein, the term "analogue" refers to a compound which exhibits an amino acid sequence with at least 75% identity to the peptide, preferably with at least 80% identity to the peptide, especially preferred with at least 85% identity to the peptide.

As used herein, the term "antagonist" refers to a compound which binds a peptide receptor without triggering a signaling cascade.

Merlo et al., Raderer et al. and Kaltsas et al. describe somatostatin analogues, in particular octreotide, octreotate and lanreotide and their somatostatin receptor binding (Merlo et al. 1999, Raderer et al. 2000, Kaltsas et al. 2005). In an embodiment, the somatostatin analogue is octreotide, octreotate or lanreotide.

Wild et al. 2011 describes a somatostatin antagonist, in particular pNO$_2$-Phe-c($_D$Cys-Tyr-$_D$Trp-Lys-Thr-Cys)$_D$TyrNH$_2$ (BASS) and its somatostatin receptor binding (Wild et al. 2011). Gonzalez et al. describes bombesin, gastrin-releasing peptide (GRP), neuromedin B and their analogues (Gonzalez et al. 2008). Furthermore, Ohki-Hamazaki et al. describes bombesin, gastrin-releasing peptide (GRP), neuromedin B and their analogues, in particular the bombesin analogue alytesin (Ohki-Hamazaki et al. 2005).

Hessenius et al. and Raderer et al. 2000 describe the vasoactive intestinal peptide (VIP) and their binding to VIP receptors (Hessenius et al. 2000, Raderer et al. 2000).

Chen et al. and Yang et al. describe α-melanocyte-stimulating hormone (α-MSH), α-MSH analogues and their receptor binding (Chen et al. 2002, Yang et al. 2009). In an embodiment, MSH analogues are selected from cyclized α-MSH, melanotan I or melanotan II.

Froberg et al. and Kolenc-Peitl et al. describe DOTA conjugated cholecystokinin (CCK)-2 and gastrin and their receptor binding (Froberg et al. 2009, Kolenc-Peitl et al. 2011).

De Visser et al. and Buchegger et al. describe neurotensin analogues, in particular DOTA and DTPA conjugated neurotensin analogues and a hexapeptide analogue of the carboxy-terminus of neurotensin (de Visser et al. 2003, Buchegger et al. 2003).

Reubi et al. describes the effect of neuropeptide Y (NPY) and neuropeptide Y analogues and their receptor binding in cancer (Reubi et al. 2001).

Nagy and Schally and Popovics et al. describe luteinizing hormone-releasing hormone (LHRH) and a cytotoxic LHRH conjugate and their receptor as specific target for cancer therapy (Nagy and Schally 2005, Popovics et al. 2014).

Beaujouan et al. describes tachykinins or neurokinins, respectively, in particular substance P, neurokinin A and B (NKA and NKB) and neuropeptide Y and K (NPY and NPK) and their receptors (Beaujouan et al. 2004).

Wild et al. and Brom et al. describe Exendin-3, Exendin-4, their conjugates and their binding to glucagonlike peptide-1 (GLP-1) receptor (Wild et al. 2006, Wild et al. 2010, Brom et al. 2010).

Haubner et al., Decristoforo et al. and Dumont et al. describe Arg-Gly-Asp (RGD) peptide conjugates for the binding of αvβ3 integrin (Haubner et al. 2005, Decristoforo et al. 2008, Dumont et al. 2011).

Arap et al. describes the Arg-Gly-Asp (RGD) peptide and the Asn-Gly-Arg (NGR) peptide, conjugates with the peptides and their binding on cancer cells (Arap et al. 1998).

In an embodiment, peptides with binding specificity to membrane receptors have a binding specificity to membrane receptors selected from cluster of differentiation (CD) molecules, cytokine and chemokine receptors, tyrosine-kinase receptor family members, members of the epidermal growth factor receptor family, members of the ephrin receptor family, so called prostate specific antigens, embryonic and onco-fetal antigens, members of the vascular endothelia growth factor receptor family, members of the mucin protein family, folate binding proteins and receptors, ligands of the NKG2D receptor, members of the epithelial glycoprotein (EGP) family, disialogangliosides, members of the carbonic anhydrase family, and members of the carbohydrate antigen family, lectins, lectin-like molecules, members of the tumor-necrosis factor receptor family, members of the keratin family and mutants of the membrane receptors.

As used herein, the term "mutants" refers to membrane receptors having at least 75% identity in the extracellular region, preferably at least 90%.

In a preferred embodiment, peptides with binding specificity to membrane receptors have a binding specificity to membrane receptors selected from CD2, CD3, CD4, CD8, CD10, CD13, CD19, CD20, CD22, CD23, CD30, CD25, CD33, CD38, CD44, CD52, CD90, CD99, CD123, CD181, CD182, CD184, CD223, CD269, CD274, CD276, CD279 and CD366, interleukin receptors, especially preferred IL-8Ra (CXCR1), IL-8Rp (CXCR2), IL-11Ra, IL-11Rp, IL-13Ral and 2, CXCR4; c-Met, transforming growth factor β receptors, ErbB1, ErbB2, ErbB3, ErbB4 and mutants thereof, ephrin receptors, especially preferred EphA1-10 or EphB1-6; prostate stem cell antigen (PSCA), prostate specific membrane antigen (PSMA), embryonic antigens (e.g. carcinoembryonic antigen CEA, fetal acethylcholine receptor), onco-fetal antigens, tumor-specific glycans [e.g. serine- or threonine-linked N-acetylgalactosamine (Tn) or derivatives like sialyl-Tn]; VEGFR 1, VEGFR 2 or VEGFR 3, Neuropilin-1, epithelia cell adhesion molecule (EpCAM), epidermal growth factor receptor (EGFR), alphafetoprotein (AFP), mucins, especially preferred MUC1, MUC16 or MUC18; follicle stimulating hormone receptor (FSHR), human high molecular weight-melanoma-associated antigen (HMW-MAA), folate binding protein (FBP), a folate receptor, NKG2D, major histocompatibility complex (MHC) class I molecules, especially preferred MHC class I chain-related gene A (MICA) or B (MICB), UL16 binding protein (ULPB) 1, ULPB 2, ULPB 3, ribonucleic acid export 1 (Rae-1) family members or histocompatibility 60 (H-60); chaperones and heat shock proteins, especially preferred heat shock protein (HSP) 90 or 78 kDa glucose-regulated protein (GRP78); EGP-2 or EGP-4, diasialoganglioside 2 (GD2) or GD3, carbonic anhydrase 9 (CAIX), Lewis Y (LeY), C-type lectin-like molecule-1 (CLL-1), tumor necrosis factor related apoptosis inducing ligand (TRAIL) receptor, apoptosis antigen 1 (APO-1, Fas, CD95), Notch ligands (e.g. Delta-like 1 and 4), members of the keratin family or integrins, especially preferred avβ3 or avβ5, aminopeptidase A, aminopeptidase N or neural/glial antigen 2 (NG2).

Clark-Lewis et al. describes interleukin-8 (IL-8) and IL-8 analogues and their binding capacity to specific membrane receptors on neutrophils (Clark-Lewis et al. 1991).

Cardó-Vila et al. describes interleukin-11 (IL-11) and IL-11 analogues and their binding capacity to the IL-11 receptor, e.g. on the surface of tumor cells (Cardó-Vila et al. 2008).

Sai et al. describes a peptide specifically binding to interleukin-13 receptor subunit alpha 2 (Sai et al. 2017).

Hanaoka et al. describes the design of a 14-residue peptide as inhibitor for the chemokine receptor CXCR4, the synthesis of a DTPA conjugate of the peptide and the receptor binding (Hanaoka et al. 2006). Furthermore, Jacobson et al. describes the development of a highly selective CXCR4 antagonist based on a short peptide (Jacobson et al. 2010). Laverman et al. discloses receptor-binding peptides, in particular targeting receptors overexpressed on tumor cells. Laverman et al. discloses CKK peptides, GLP-1 peptides, CXCR4-binding peptides and Gastrin-releasing peptide receptor-targeting peptides (BN, GRP and BN analogues) (Laverman et al. 2012).

Broda et al. describes the c-Met binding peptide cMBP2 and a method to select suitable binding peptides to receptors, in particular on tumor cells (Broda et al. 2015).

Wang et al. describes a conjugate of an erbB2 binding peptide (LTVSPWY) (Wang et al. 2007a).

Kolonin et al. and Staquicini et al. describe peptide ligands to the ephrin receptor EphA5 for targeting human cancer cells (Kolonin et al. 2006, Staquicini et al. 2015).

Barrett et al., Vallabhajosula et al. and Afshar-Oromieh et al. describe peptides binding prostate specific membrane antigen (PSMA) (Barrett et al. 2013, Vallabhajosula et al. 2014, Afshar-Oromieh et al. 2015). Furthermore, WO 2010/108125 A2 and WO 2015/055318 A1 disclose PSMA-binding peptides.

De Rosa et al. describes the design and synthesis of peptides showing a VEGF-like receptor binding to the receptor VEGFR2 (De Rosa et al. 2016). Michaloski et al. describes peptides that bind to all VEGFRs (Michaloski et al. 2016).

Karjalainen et al. describe a peptide binding to Neuropilin-1 (Karjalainen et al. 2011).

Iwasaki et al. 2015 describe a 14-mer macrocyclic peptide binding to the extracellular domain of epithelia cell adhesion molecule (EpCAM) (Iwasaki et al. 2015).

Cardó-Vila et al. 2010 describes a peptide binding to EGFR (Caro-Vila et al. 2010).

Staquicini et al. 2008 describes MUC18-derived 9-mer and 10-mer peptides binding to MUC18, mimicking its homophilic interaction (Staquicini et al. 2008).

Arap et al. describes the stress response chaperon GRP78 binding peptides motifs and synthetic chimeric peptides comprising the GRP78 binding motifs for targeting tumor cells (Arap et al. 2004) and Vidal et al. describes a peptide binding to HSP90 (Vidal et al. 2004).

Kajiwara et al. describes a method for the design of synthetic peptides binding to receptors, in particular the design and synthesis of synthetic peptides binding members of the tumor-necrosis factor receptor family, TRAIL (tumor necrosis factor related apoptosis inducing ligand receptor), TNFR1 or Fas (apoptosis antigen 1, APO-1, CD95) (Kajiwara et al. 2004).

Soudy et al. describes two peptides, 12-mer and 10-mer, and their conjugates binding keratin 1, a member of the keratin family (Soudy et al. 2017).

Cardo-Vila et al. describes a avβ5-binding peptide (Cardo-Vila et al. 2003).

Marchio et al. describes a peptide targeting Aminopeptidase A (Marchio et al. 2004). Pasqualini et al. describes the targeting of a drug to aminopeptidase N (CD13) via an NGR peptide tag (Pasqualini et al. 2000).

Burg et al. describes peptides targeting NG2 on neovasculature (Burg et al. 1999).

Preferably, the peptides with binding specificity to membrane receptors are selected from the group disclosed by Clark-Lewis et al., Cardó-Vila et al. (2003/2008/2010), Sai et al., Hanaoka et al., Jacobson et al., Laverman et al., Broda et al., Wang et al., Kolonin et al., Staquicini et al. (2008/2015), Barrett et al., Vallabhajosula et al. and Afshar-Oromieh et al., De Rosa et al., Michaloski et al., Karjalainen et al., Iwasaki et al., Arap et al., Kajiwara et al., Soudy et al., Marchio et al., Pasqualini et al. or Burg et al.

In a preferred embodiment, the chemically synthesized peptide binding moiety is selected from somatostatin, bombesin, gastrin-releasing peptide (GRP), vasoactive intestinal peptide (VIP), α-melanocyte-stimulating hormone (α-MSH), melanotan 2 (α-M2), cholecystokinin (CCK) or gastrin, neurotensin, neuropeptide Y, luteinizing hormone-releasing hormone (LHRH), substance P, Exendin, Arg-Gly-Asp (RGD) peptide or Asn-Gly-Arg (NGR) peptide.

In an embodiment, the targeting module is a peptide comprising 13 to 85 amino acids, especially preferred 20 to 60 amino acids.

In an embodiment, the chemically synthesized peptide binding moiety is a peptide with 3 to 75 amino acids, preferred 10 to 50 amino acids.

In a further embodiment, the chemically synthesized peptide binding moiety comprises one peptide (monospecific), two, three or more peptides (bi- and multispecific).

In a further embodiment, the chemically synthesized peptide binding moiety comprises at least two peptides selected from somatostatin and somatostatin analogues, somatostatin antagonists, bombesin and bombesin analogues, gastrin-releasing peptide (GRP) and GRP analogues, neuromedin B and neuromedin B analogues, vasoactive secretin family, melanocyte-stimulating hormones (MSH) and MSH analogues, cholecystokinins (CCK), gastrins, neurotensin and neurotensin analogues, gonadotropin-releasing hormone family, neurokines, exendins or exenatides, Arg-Gly-Asp (RGD) peptides and Asn-Gly-Arg (NGR) peptides, neuregulins or peptides with binding specificity to membrane receptors.

Examples for a chemically synthesized peptide binding moiety with at least two peptides include, but are not limited to, a combination of two different peptides binding to the same cell surface protein (e.g. IL-11R, IL-13RA2, ErbB2, PSCA, PSMA, VEGFR or GD2), a combination of a PSMA-binding peptide and peptides binding to VEGFR-2, PSCA, IL-11R or MUC1, combinations of peptides binding to GD2 and CD90 or a combination of melanotan I and II, their analogues or the circularized peptides.

In a further embodiment, the chemically synthesized peptide binding moiety and/or the tag comprise D amino acids, pseudo peptide bonds, amino alcohols, non-proteinogenic amino acids, amino acids with modified side chains and/or the chemically synthesized peptide binding moiety and/or the tag are circularized peptides.

According to the invention, the tag is a peptide from any protein, against which an antibody or other binding domain is available.

In further embodiments, the tag is a peptide from any human protein, against which an antibody or other binding domain is available.

In further embodiments, the tag is a peptide from a human nuclear protein, against which an antibody or other binding domain is available.

The invention comprises further the use of target modules according to the invention for preparing a medication for therapeutic and/or diagnostic use in case of cancer or an autoimmune disease.

The invention also encompasses a method for treatment of a human having cancer, infectious, inflammatory or an autoimmune disease by administration of target modules according to the invention.

For therapeutic applications, a sterile pharmaceutical composition, containing a pharmacologically effective quantity of target modules according to the invention, is administered to a patient in order to treat the aforementioned illnesses.

The invention will be explained in more detail with the aid of the following figures and embodiments without limiting the invention to them.

The present invention will now be further explained by the following non-limiting figures and examples.

FIG. 1 shows a schema of the modular composition of the UniCAR platform and mode of action of UniCAR platform by binding of target specific peptide targeting modules (pTM) to target structures on the surface of a target cell, for example tumor cell as in the scheme.

FIG. 2 shows a schema of an universal chimeric antigen receptor (UniCAR) with three domains, wherein the first domain is a tag-binding domain (e.g. scFv anti tag), the second domain is an extracellular hinge (ECD) and a transmembrane domain (TMD) and the third domain is a signal transduction domain (ICD), and the optional fourth domain is a short peptide linker in the extracellular portion of the receptor (not shown).

FIG. 3 shows the vector pLVX-EF1alpha UniCAR 28/ζ (Clontech, Takara Bio Group) with 5' long terminal repeat (5' LTR), primer binding site (PBS), packaging signal (ψ), Rev-response element (RRE), central polypurine tract/central termination sequence (cPPT/CTS), human elongation factor 1 alpha promoter (PEF1a), multiple cloning site (MCS), internal ribosome entry site (IRES), human-codon-optimized (ZsGreen1), woodchuck hepatitis virus posttranscriptional regulatory element (WPRE), 3' long terminal repeat (3' LTR), origin of replication (pUC), ampicillin resistance gene (Ampr), β-lactamase.

Figure 6:
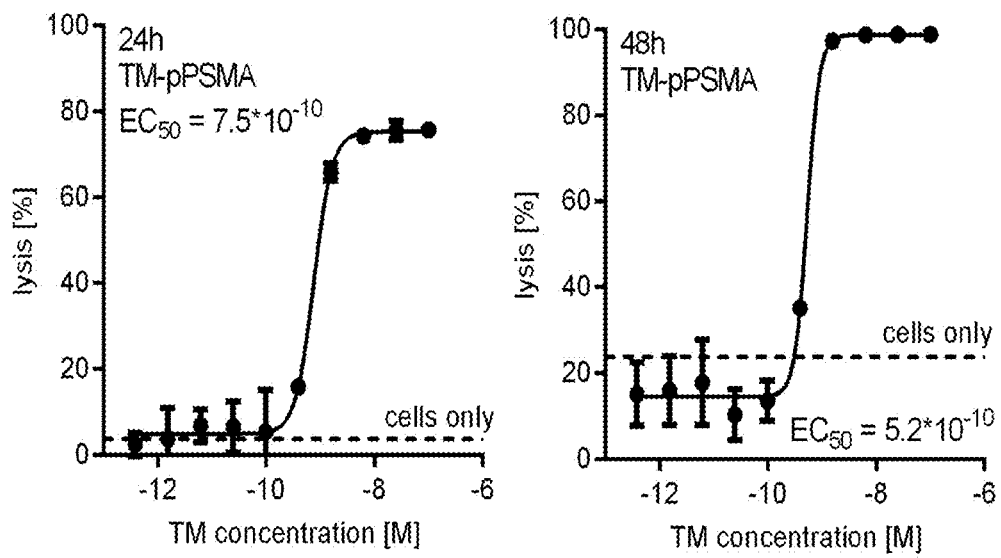

FIG. 6 shows peptide targeting module dose-dependent cytotoxic activity of human native T cells genetically engineered to express UniCAR towards prostate specific membrane antigen (PSMA) expressing target cells (OCI-AML3 genetically engineered to express PSMA) in the presence of a PSMA-specific peptide targeting module (TM-pPSMA). Lysis relative to control samples with only target cells after 24 h and 48 h incubation time is shown. For control of alloreactivity UniCAR-T were incubated with target cells in absence of TM-pPSMA (cells only).

Figure 7:
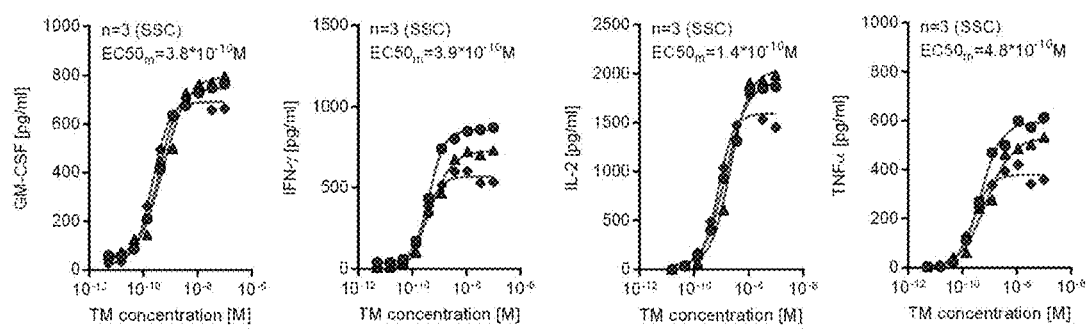

FIG. 7 shows peptide targeting module dose-dependent secretion of T cell specific cytokines (Granulocyte-macrophage colony-stimulating factor GM-CSF, interferon gamma IFN-γ, interleukin 2 IL-2, and tumor necrosis factor alpha TNF☐) of human native T cells genetically engineered to express UniCAR upon establishment of an immune synapse to target cells by peptide targeting modules.

Figure 8:
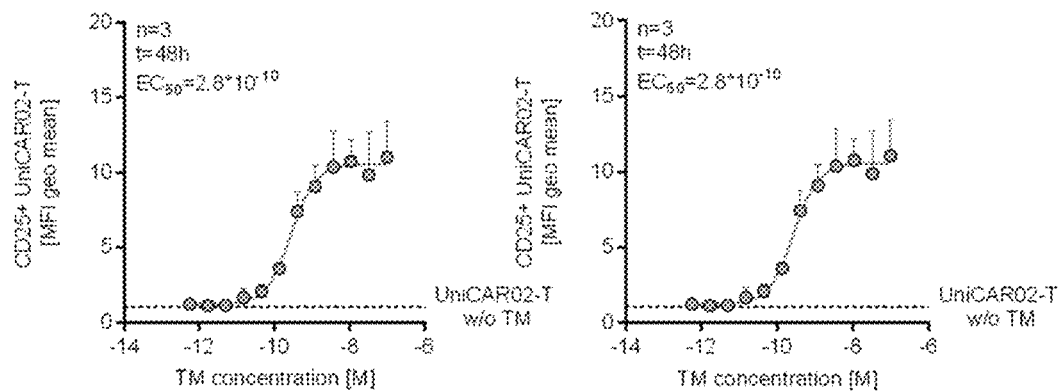

FIG. 8 shows peptide targeting module dose-dependent activation of human native T cells genetically engineered to express UniCAR as determined by activation marker CD25 surface expression upon establishment of an immune synapse to target cells by peptide targeting modules.

Figure 9:
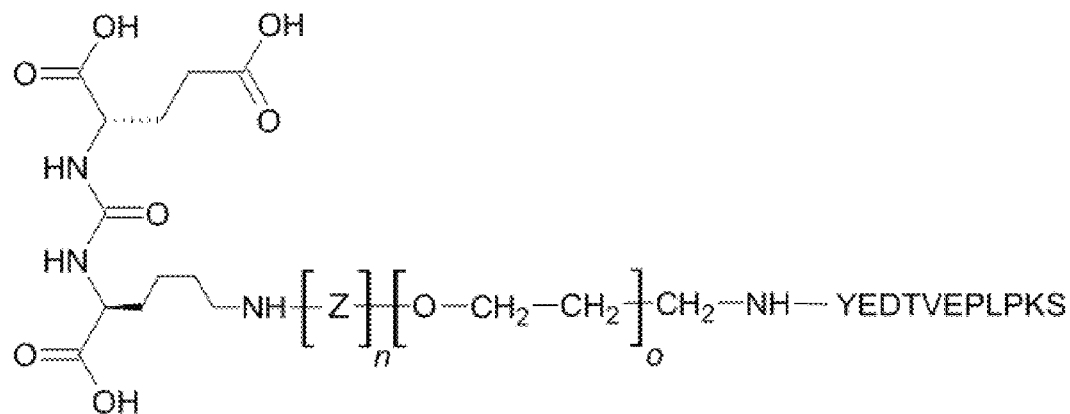

FIG. 9 depicts a targeting module according to the invention binding to PSMA, including a PSMA binding glutamate-urea-lysine motif, followed by Z being a single chelator [i.e. a N,N-bis(2-Hydroxybenzyl)ethylenediamine-N,N-diacetic acid (HBED) chelator] or aromatic amino acid or multiple thereof and O being a linker of 2 or more repeats (i.e. PEG linker) connected to the La 5B9 epitope (SEQ ID NO: 28).

Figure 10:
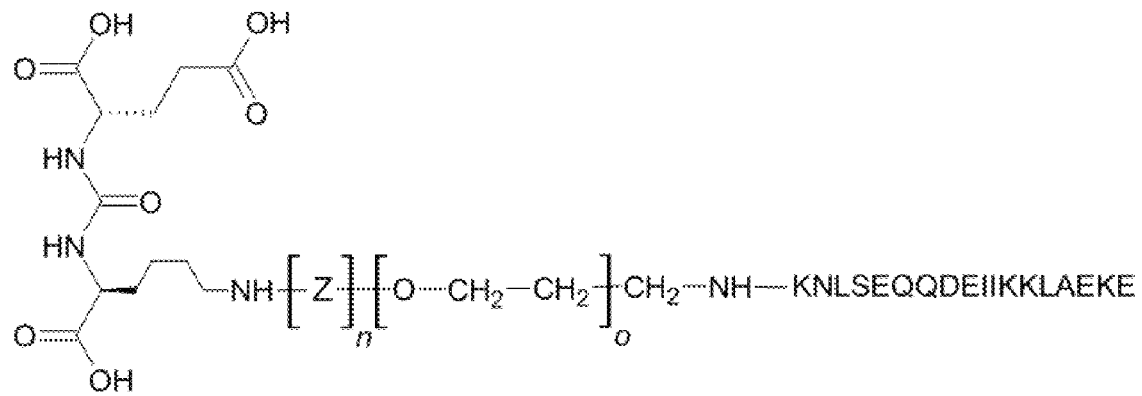

FIG. 10 depicts a targeting module according to the invention binding to PSMA, including a PSMA binding glutamate-urea-lysine motif, followed by Z being a single chelator [i.e. a N,N-bis(2-Hydroxybenzyl)ethylenediamine-N,N-diacetic acid (HBED) chelator] or aromatic amino acid or multiple thereof and O being a linker of 2 or more repeats (i.e. PEG linker) connected to the La 7B6 epitope (SEQ ID NO: 27).

In preferred embodiments, the tag is a peptide from the human nuclear La protein. In an embodiment, the peptide from the human nuclear La protein is selected from short linear epitopes recognized by the monoclonal anti-La antibodies 5B9 or 7B6. Preferably, the tag is a short linear epitope from the human nuclear La protein (E5B9) according to SEQ ID NO: 25 or from the E7B6 epitope according to SEQ ID NO: 27.

In further embodiments, the targeting module according to the invention further comprises at least one additional ligand. Additional ligands are not involved in the target antigen binding. In an embodiment, at least one additional ligand is selected from costimulatory ligands or cytokines fused to the N- or C-terminus of the targeting module, preferably the extracellular domain of CD28, CD137 (41BB), CD134 (OX40), CD27 or IL-2, IL-7, IL-12, IL-15, IL-17 and 11-21. In further embodiments, the at least one additional ligand is selected from chemical compounds which induce cell death in the target and neighboring cells.

In further embodiments, the targeting module according to the invention further comprises a chelator. As used herein, the term "chelator" refers to a compound which forms two or more separate coordinate bonds with one metal ion. In an embodiment, the chelator is selected from diethylenetriaminepentaacetic acid (DTPA), 1,4,7,10-Tetraazacyclododecane-N,N',N'',N'''-tetraacetic acid (DOTA), mercaptoacetyltriglycine (MAG3), 6-Hydrazinopridine-3-carboxylic acid (Hynic), hydroxybenzyl ethylenediamine (HBED), N,N'-bis [2-hydroxy-5-(carboxyethyl)benzyl]ethylenediamine-N,N'-diacetic acid (HBED-CC) or 2-(3-(1-carboxy-5-[(6-fluoro-pyridine-3-carbonyl)-amino]-pentyl)-ureido)-pentanedioic acid (DCFPyL).

In preferred embodiments, the targeting module according to the invention comprises a chelator at the C-terminus.

In embodiments, the targeting module according to the invention comprising a chelator further comprises a metal or metal ion, preferably a radionuclide. The term "radionuclide" refers to an atom that has excess nuclear energy, making it unstable. In an embodiment, the radionuclide is selected from $^{51}$Cr, $^{89}$Sr, $^{90}$Y, $^{99m}$Tc, $^{111}$In, $^{133}$Xe, $^{153}$Sm, $^{169}$Er, $^{186}$Re, $^{201}$Tl or $^{224}$Ra.

In embodiments, the targeting module according to the invention comprising a chelator is used for the preparation of a radiolabeled compound.

In embodiments, the targeting module according to the invention binds to PSMA and has a structure according to Formula (I), including a PSMA binding glutamate-urea-lysine motif, followed by a short linker and a N,N-bis(2-Hydroxybenzyl)ethylenediamine-N,N-diacetic acid (HBED) chelator. A PEG linker is connected to the chelator followed by the La 5B9 epitope.

Formula (I)

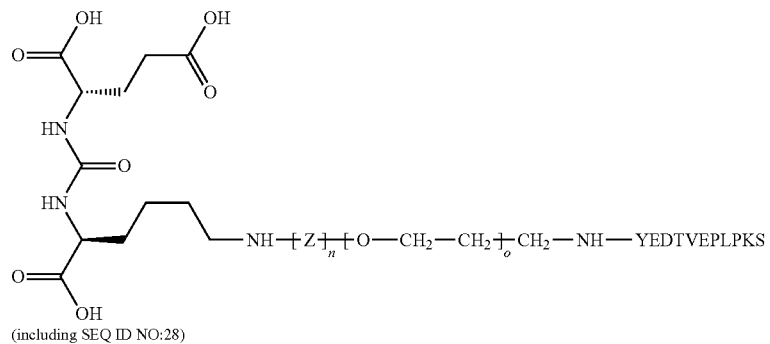

(including SEQ ID NO:28)

In embodiments, the targeting module according to the invention binds to PSMA and has a structure according to Formula (II), including a PSMA binding glutamate-urea-lysine motif, followed by a short linker and a N,N-bis(2-Hydroxybenzyl)ethylenediamine-N,N-diacetic acid (HBED) chelator. A PEG linker is connected to the chelator followed by the La 7B6 epitope.

Formula (II)

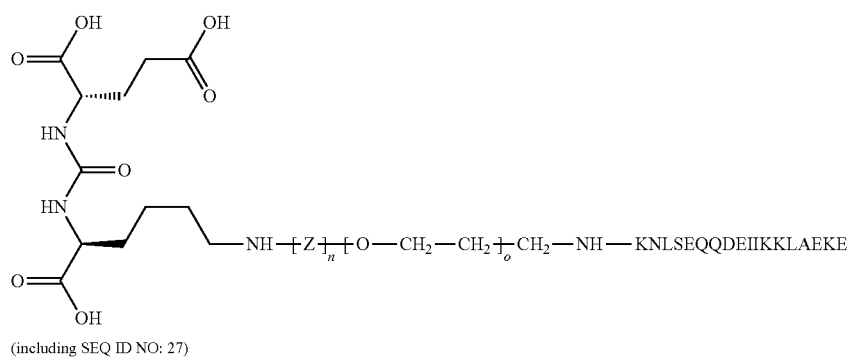

(including SEQ ID NO: 27)

In embodiments, the targeting module according to the invention binds to IL13RA2 and has a structure according to SEQ ID NO: 26, including a IL13RA2 binding motif, followed by a linker and the La 5B9 epitope.

Targeting Module Production

Peptide targeting modules (pTMs) comprise two domains, a binding moiety specific for a certain human cell surface protein or protein complex and a tag, which is recognized by the binding moiety of the UniCAR. pTMs can be manufactured by techniques known to the skilled artisan. These techniques include, but are not limited to, artificial synthesis of polypeptide chains or solid-phase and solution-phase chemical synthesis.

In one aspect, a pTM may be synthesized in a single, two or multiple solution-phase chemical synthesis procedure. As a first step a 1-(9-fluorenylmethyloxycarbonyl-amino)-4,7,10-trioxa-13-tridecanamine hydrochloride (Fmoc-TOTA*HCl) linker molecule is dissolved in dichloromethane (DCM) with N,N diisopropylethylamine (DIPEA) and loaded onto 2-chlorotrityl polystyrene resin (2-chlorotrityl PS). Thereby Fmoc-TOTA*HCl is covalently linked to the resin for further processing. To block the unreacted 2 chlorotritylchlorids of 2-chlorotrityl chloride resin, a capping solution consisting of methanol and DIPEA in DCM can be used. Afterwards the covalently linked structure 4,7,10-trioxa-13-tridecanamine (TOTA) which later functions as linker in the final molecule is deprotected from its fluorenylmethyloxycarbonyl (Fmoc) protecting group using 20% piperidine in dimethylformamide (DMF). Next, fluorenylmethyloxycarbonyl/tert-Butyl (Fmoc/tBu)-strategy can be used to add amino acids sequentially to fixed TOTA. Single amino acids are protected by corresponding protecting groups. Coupling can takes place with N,N'-diisopropylcarbodiimide (DIC) and ethyl 2-cyano-2-hydroxyimino)acetate (Oxyma Pure) in DMC/N-Methyl-2-pyrrolidone (NMP) or using Boc-O-tert-butyl-L-serine (dicyclohexylammonium) salt (Boc-Ser(tBu)-OH*DCHA) and benzotriazol-1-yl-oxytripyrrolidinophosphonium hexafluorophosphate (PyBOP) as coupling reagent. In this way, amino acid chains of varying length from 2 to 100 can be generated. The constructed peptide with its TOTA linker is cleaved from the resin using hexafluoroisopropanol (HFIP) in dimethyl carbonate (DCM). Protecting groups of side groups and N-terminal tert-butyloxycarbonyl (Boc) are unaffected. DCM is used as solvent.

HPLC process is used to replace to the trifluoroacetic acid (TFA) counter-ion with acetate counter-ion followed by a final freeze drying.

Final products can be purified using high performance liquid chromatography (HPLC). In particular, reversed-phase HPLC can be helpful. A common purification buffer is TFA.

Alternatively or additionally ion exchange chromatography can be applied to purify final peptide products.

In further embodiments, the targeting module according to the invention is used in the treatment of cancer, infections, inflammatory and autoimmune disorders.

In a further aspect the present invention further comprises a kit comprising
a) at least one targeting module according to the invention and
b) a vector or a cell comprising a nucleic acid encoding a universal chimeric antigen receptor,
wherein the universal chimeric antigen receptor comprises three domains,
wherein
the first domain is a tag-binding domain,
the second domain is an extracellular hinge and a transmembrane domain and
the third domain is a signal transduction domain,
wherein tag-binding domain binds to the tag of the targeting module according to the present invention.

Figure 1:
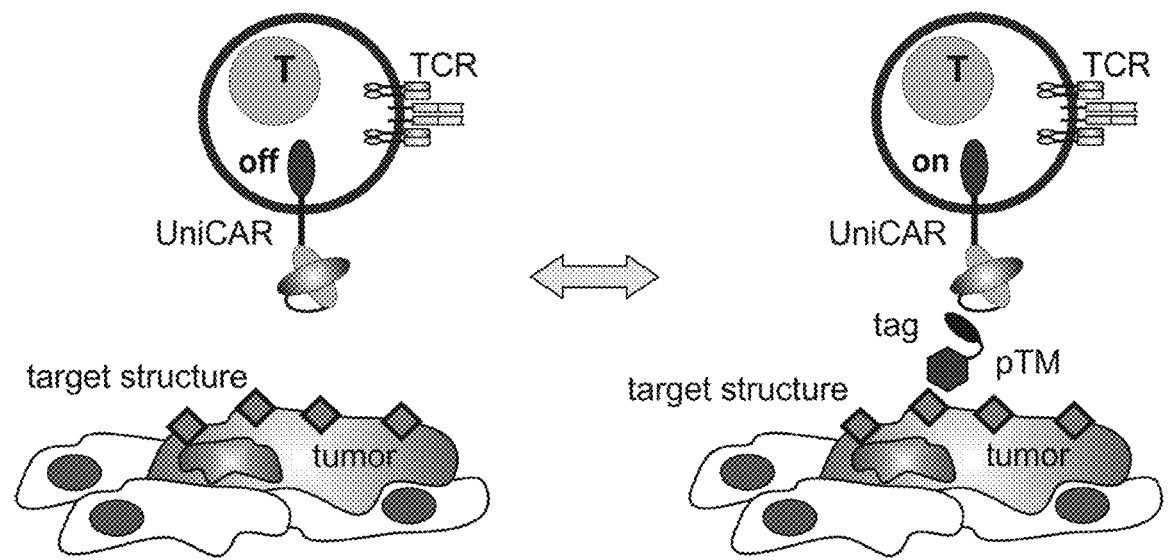
Figure 2:
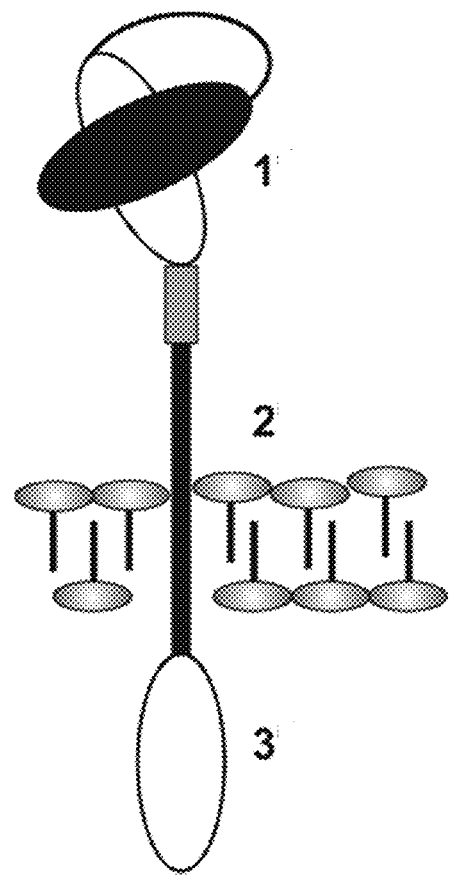

As used herein, the term "universal chimeric antigen receptor" refers to an artificial chimeric fusion protein, in particular a receptor comprising a tag-binding domain, an extracellular hinge and a transmembrane domain and a signal transduction domain (FIG. 2). The domains can be derived from different sources and therefore, the receptor is called chimeric. Advantageously, the receptor can bind with the tag-binding domain to different targeting modules and therefore is universal.

Advantageously, the cell comprising a nucleic acid encoding a universal chimeric antigen receptor (UniCAR) expresses the UniCAR, which has binding specificity for the tag of the targeting module, which in turn binds to a cellular surface protein or an extracellular structure.

As used herein, the term "domain" refers to a part of a protein sequence, which can exist and function independently from the rest of the protein.

In embodiments, the kit comprises at least two targeting modules according to the invention, wherein the at least two targeting modules comprise different chemically synthesized peptide binding moieties specific for a human cell surface protein or protein complex, and the same tag, wherein the tag is a peptide from a human nuclear protein.

In embodiments, the kit comprises one to five targeting modules according to the invention, preferably one to three targeting modules.

In embodiments, the tag-binding domain is present at the amino terminal end of the polypeptide that comprises the UniCAR. Advantageously, locating the tag-binding domain at the amino terminus permits the tag-binding domain unhampered access to the tagged targeting module that is bound to the target cell.

In further embodiments, the tag-binding domain is an antibody or an antigen-binding fragment. As used herein, the term "antibody" refers to a protein which binds antigens via the Fab's variable region. The fragment antigen-binding (Fab) fragment is a region on an antibody that binds to antigens. It is composed of one constant and one variable domain of each of the heavy and the light chain. As used herein, the term "antigen-binding fragment" refers to a protein comprising at least the variable domain of a light or heavy chain of an antibody. In an embodiment, antigen-binding fragments are selected from single-chain variable fragment (scFv), single chain antibodies, F(ab')2 fragments, Fab fragments, and fragments produced by a Fab expression library.

In embodiments, the tag-binding domain is obtained from an animal species, preferably from a mammal such as human, simian, mouse, rat, rabbit, guinea pig, horse, cow, sheep, goat, pig, dog or cat. Preferably, the tag-binding domain is a human or humanized antibody.

In embodiments, the tag-binding domain is a polyclonal, monoclonal, or chimeric antibody, wherein an antigen binding region of a non-human antibody is transferred into the framework of a human antibody by recombinant DNA techniques.

In embodiments, antibodies to a selected tag may be produced by immunization of various hosts including, but not limited to, goats, rabbits, rats, mice, humans, through injection with a particular protein or any portion, fragment or oligopeptide that retain immunogenic properties of the protein.

In embodiments, the tag-binding domain binds to a tag from a human nuclear La protein, preferably the tag-binding domain is an antibody or an antigen-binding fragment, wherein the tag-binding domain constitutes an anti-La epitope scFv, more preferably an anti-La epitope scFv according to SEQ ID NO: 21 and 22 or 23 and 24.

Advantageously, tags are peptide sequences from nuclear antigens, which cannot be accessed and bound by the corresponding tag-binding domain in the context of the native protein under physiological conditions. Furthermore advantageously, the tag is not immunogenic. This leads to minimization of risk of uncontrolled on-target off-site toxicities by UniCAR expressing immune cells like release of toxic levels of cytokines, referred to variously as cytokine storms or cytokine release syndrome (CRS).

As used herein, the term "single chain variable fragment (scFv)" refers to an artificial antigen-binding fragment comprising a variable domain of a light and a heavy chain of an antibody covalently linked. In an embodiment, the variable domain of a light (VL) and a heavy chain (VH) of an antibody are covalently linked by a short peptide of ten to 25 amino acids. In a further embodiment, the short peptide links the N-terminus of the VH with the C-terminus of the VL, or vice versa.

As used herein, the term "extracellular hinge" refers to a flexible peptide sequence connecting the tag-binding domain and the transmembrane domain, which allows the UniCAR to protrude from the surface of the cell for optimal binding to its particular tag.

As used herein, the term "transmembrane domain" refers to a peptide sequence which is thermodynamically stable in a membrane and therefore, anchors the UniCAR into the cell membrane of the cell.

In a further embodiment, the extracellular hinge and transmembrane domain is selected from hinge and transmembrane domains of human CD28 molecule, CD8a chain, NK cell receptors, preferably natural killer group NKG2D; or parts of the constant region of an antibody and combinations thereof. As used herein, the term "combinations thereof" refers to combinations of different hinge and transmembrane domains.

Pinthus et al. 2003, Pinthus et al. 2004, Cartellieri et al. 2014 and Cartellieri et al. 2016 describe the use of hinge and transmembrane domains of human CD28 molecule in CARs (Pinthus et al. 2003, Pinthus et al. 2004, Cartellieri et al. 2014, Cartellieri et al 2016).

Carpentino et al., Milone et al. and Zhao et al. describe the use of hinge and transmembrane domains of human CD8a molecule in CARs (Carpentino et al. 2009, Milone et al. 2009, Zhao et al. 2009).

Zhang et al. 2005 and Zhang et al. 2006 describe the use of hinge and transmembrane domains of NKG2D in CARs (Zhang et al. 2005, Zhang et al. 2006).

Hombach et al., Frigault et al. and Wang et al. describe the use of hinge and transmembrane domains of parts of the constant region of immunoblobulin G1 (IgG) (Hombach et al. 2007, Frigault et al. 2015, Wang et al. 2007b). Frigault et al. describes the use of hinge domains of the constant region of IgG4.

Examples of combinations of the extracellular hinge and transmembrane domain are, but are not limited to, CD28 extracellular hinge and transmembrane domain, CD8alpha extracellular hinge and transmembrane domain, IgG1 or IgG4 constant regions combined with CD28 or CD137 transmembrane domain.

As used herein, the term "signal transduction domain" refers to an amino acid sequence which transmits a signal into the cell by cross-linkage of the cell expressing the UniCAR (effector cell) to a human cell surface protein or protein complex (target cell). Cross-linkage between effector and target cell is mediated by the targeting module according to the invention.

In further embodiments, the signal transduction domain is selected from cytoplasmic regions of CD28, CD137 (4-1BB), CD134 (OX40), DAP10 and CD27, programmed cell death-1 (PD-1), cytotoxic T-lymphocyte antigen 4 (CTLA-4), cytoplasmic regions of CD3 chains, DAP12 and activating Fc receptors.

Hombach et al., Maher et al. and Cartellieri et al. describe the use of cytoplasmic regions of CD28 as signal transduction domain in CARs (Hombach et al. 2001, Maher et al. 2002, Cartellieri et al. 2014, Cartellieri et al. 2016).

Milone et al. and Finney et al. describe the use of cytoplasmic regions of CD137 (4-1BB) as signal transduction domain (Finney et al. 2004, Milone et al. 2009).

Finney et al., Hombach and Abken 2011 and Hombach and Abken 2013 describe the use of cytoplasmic regions of CD134 (OX40) as signal transduction domain in CARs (Finney et al. 2004, Hombach and Abken 2011, Hombach and Abken 2013).

Zhang et al. describes the use of DAP10 as signal transduction domain (Zhang et al. 2005).

Fedorov et al. describes the use of programmed cell death 1 (PD-1) and of cytotoxic T-lymphocyte antigen 4 (CTLA-4) as signal transduction domain in CARs (Fedorov et al. 2013).

Gong et al. and Gade et al. describe the use of cytoplasmic regions CD3 chains, in particular the CD3Cζ chain, as signal transduction domain in CARs (Gong et al. 1999, Gade et al. 2005).

Töpfer et al. describes the use of DAP12 as signal transduction domain in CARs (Topfer et al. 2015).

Lamers et al. and Kershaw et al. describe the use of activating Fc receptors, in particular the Fc epsilon receptor γ chain, as signal transduction domain (Lamers et al. 2004, Kershaw et al. 2006).

In an embodiment, the universal chimeric antigen receptor comprises at least one signal transduction domain, preferably two, three, four or more signal transduction domains, especially preferably selected from cytoplasmic regions of CD28, CD137 (4-1BB), CD134 (OX40), DAP10 and CD27, programmed cell death-1 (PD-1), cytotoxic T-lymphocyte antigen 4 (CTLA-4), cytoplasmic regions of CD3 chains, DAP12 and activating Fc receptors.

In further embodiments a nucleic acid encoding a universal chimeric antigen receptor referred to as UniCAR01 according to SEQ ID NO: 1 is provided. The nucleic acid sequence encodes a human IL-2m leader peptide according to SEQ ID NO: 2, a humanized heavy chain of an anti-La 5B9 scFv according to SEQ ID NO: 3, a humanized light chain of an anti-La 5B9 scFv according to SEQ ID NO: 4, a human CD28 portion according to SEQ ID NOs: 5 to 7, including a human CD28 extracellular part with mutated binding motif according to SEQ ID NO: 5, a CD28 transmembrane domain according to SEQ ID NO: 6, and a human CD28 intracellular part including a mutated internalization motif according to SEQ ID NO: 7, and a human CD3 zeta intracellular domain according to SEQ ID NO: 8.

The product of the protein expression of the nucleic acid according to SEQ ID NO: 1 can be obtained in SEQ ID NO: 17.

The nucleic acid sequence of humanized anti-La 5B9 variable region heavy chain according to SEQ ID NO: 3 encodes for a protein according to SEQ ID NO: 21, whereas the humanized anti-La 5B9 variable region light chain according to SEQ ID NO: 4 encodes for a protein according to SEQ ID NO: 22.

In further embodiments a nucleic acid sequence encoding an universal chimeric antigen receptor referred to as Uni-CAR02 according to SEQ ID NO: 9 is provided. The nucleic acid sequence encodes a human IL-2m leader peptide according to SEQ ID NO: 2, a humanized heavy chain of an anti-La 5B9 scFv according to SEQ ID NO: 3, a humanized light chain of an anti-La 5B9 scFv according to SEQ ID NO: 4, an extracellular hinge and a transmembrane region of the human CD8alpha chain according to SEQ ID NO: 10 and 11, a human CD137 intracellular signaling domain according to SEQ ID NO: 12, and a human CD3 zeta intracellular domain according to SEQ ID NO: 8.

The product of the protein expression of the isolated nucleic acid sequence according to SEQ ID NO: 9 can be obtained in SEQ ID NO: 18.

In further embodiments a nucleic acid encoding a universal chimeric antigen receptor referred to as UniCAR03 according to SEQ ID NO: 13 is provided. The nucleic acid sequence encodes a human IL-2m leader peptide according to SEQ ID NO: 2, a humanized heavy chain of an anti-La 7B6 scFv according to SEQ ID NO: 14, a humanized light chain of an anti-La 7B6 scFv according to SEQ ID NO: 15, a human CD28 portion according to SEQ ID NOs: 5 to 7, including a human CD28 extracellular part with mutated binding motif according to SEQ ID NO: 5, a CD28 transmembrane domain according to SEQ ID NO: 6, and a human CD28 intracellular part including a mutated internalization motif according to SEQ ID NO: 7, and a human CD3 zeta intracellular domain according to SEQ ID NO: 8.

The product of the protein expression of the nucleic acid according to SEQ ID NO: 13 can be obtained in SEQ ID NO: 19.

The nucleic acid sequence of humanized anti-7B6 variable region heavy chain according to SEQ ID NO: 14 encodes for a protein according to SEQ ID NO: 23, whereas the humanized anti-7B6 variable region light chain according to SEQ ID NO: 15 encodes for a protein according to SEQ ID NO: 24.

In a further embodiment a nucleic acid sequence encoding a reversed universal chimeric antigen receptor referred to as UniCAR04 according to SEQ ID NO: 16 is provided. The nucleic acid sequence encodes a human IL-2m leader peptide according to SEQ ID NO: 2, a humanized heavy chain of an anti-La 7B6 scFv according to SEQ ID NO: 14, a humanized light chain of an anti-La 7B6 scFv according to SEQ ID NO: 15, an extracellular hinge and a transmembrane region of the human CD8alpha chain according to SEQ ID NO: 10 and 11, a human CD137 intracellular signaling domain according to SEQ ID NO: 12, and a human CD3 zeta intracellular domain according to SEQ ID NO: 8.

The product of the protein expression of the isolated nucleic acid sequence according to SEQ ID NO: 16 can be obtained in SEQ ID NO: 20.

In a further embodiment, the universal chimeric antigen receptor comprises a fourth domain, wherein the fourth domain is a short peptide linker in the extracellular portion of the receptor.

In a further embodiment, the fourth domain forms a linear epitope for a monoclonal antibody (mab) specifically binding to the fourth domain. In an embodiment, the fourth domain comprises at least one linear epitope.

In a further embodiment, the fourth domain is located in the tag-binding domain, in between the tag-binding domain and the extracellular hinge domain or an integral part of the extracellular hinge domain.

Advantageously, the UniCAR engrafted immune cells with the fourth domain can be specifically stimulated to proliferate preferentially and persist longer compared to non-engrafted immune cells either in vitro or in vivo. Further advantageously, the fourth domain may be also used to purify UniCAR engrafted immune cells from mixed cell populations or to dampen UniCAR engrafted immune cell mediated immune response and to eliminate UniCAR engrafted immune cells in vivo.

In a further embodiment, the universal chimeric antigen receptor comprises a signal peptide. Advantageously, the signal peptide allows for expression on the cell surface of an effector cell. In an embodiment, the signal peptide is at the N-terminus of the UniCAR nuclide acid sequence in front of the tag-binding domain. In an embodiment, the signal peptide targets proteins to the secretory pathway either co-translationally or post-translationally and is selected from leader peptides from proteins like CD28, CD8alpha, IL-2 or the heavy or light chains of antibodies of human origin to avoid immunogenic reactions.

In a further embodiment, the nucleic acid is a cDNA. The term cDNA (complementary DNA) refers to double-stranded DNA synthesized from a single stranded RNA, e. g. mRNA, in a reaction catalyzed by the enzyme reverse transcriptase.

In an embodiment, the cell is selected from autologous, syngeneic or allogeneic cells, depending on the disease to be treated and the means available to do so. In an embodiment, the cell is selected from immune cells with cytolytic, phagocytic or immunosuppressive activity, such as T cells, including regulatory T cells, Natural Killer (NK) cells and macrophages. In a preferred embodiment, the cell is selected from T cells, including alpha/beta and gamma/delta T cells or subpopulations of T cells like stem-cell memory T cells or central memory T cells, cytotoxic T cells, regulatory T cells; or NK cells. In one aspect, effector cells are from a certain HLA background and utilized in an autologous or allogeneic system. Effector cells can be isolated from any source, including from a tumor explant of the subject being treated or intratumoral cells of the subject being treated. In an embodiment, effector cells may be generated by in vitro differentiation from pluri- or multipotent stem or progenitor cells prior to or after genetic manipulation of the respective cells to express UniCARs. In the following, the term "effector cell" refers to any kind of aforementioned immune cells genetically altered to express UniCARs on their cell surface.

UniCAR Cell Production

The immune cells can be genetically engineered to express UniCARs by various methods. A polynucleotide vector encoding the UniCAR and all necessary elements to ensure its expression in the genetically engineered immune cell is transferred into the immune cell. The transfer of the vector can be performed by electroporation or transfection of nucleic acids or the help of viral vector systems like adeno-, adeno-associated, retro-, foamy- or lentiviral viral gene transfer.

Figure 3:
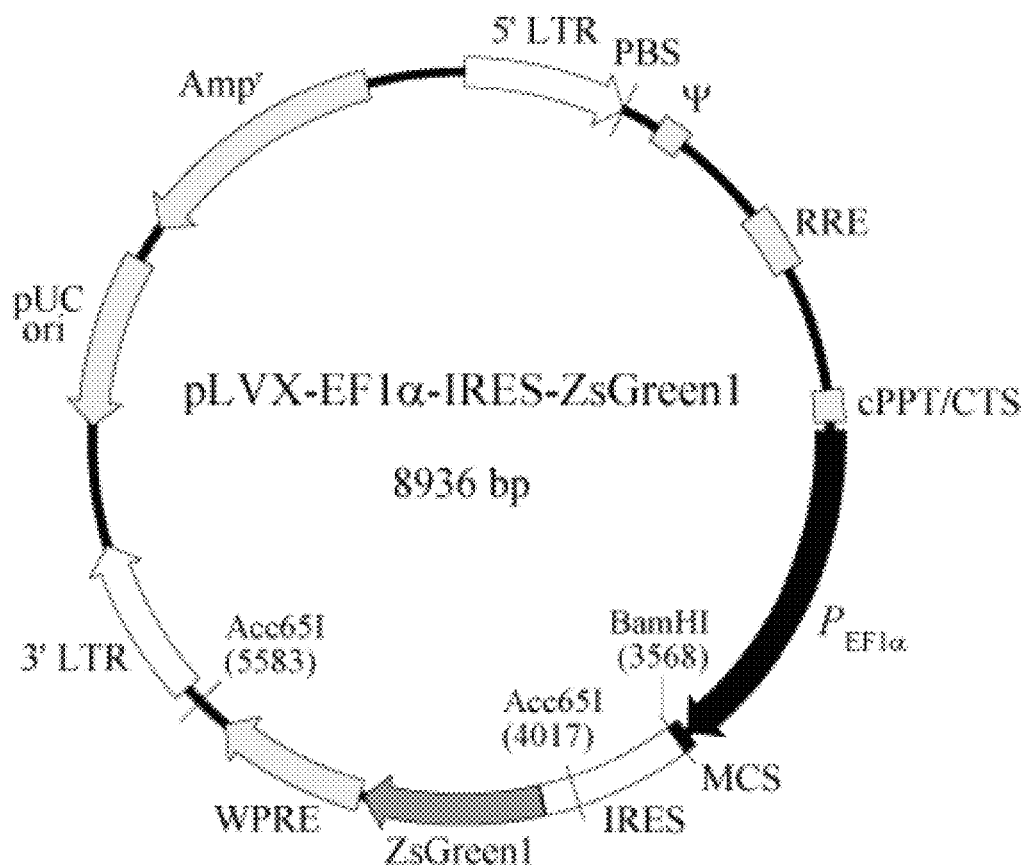

The lentiviral gene transfer is applied for stable expression of UniCARs in immune cells by first constructing a lentiviral vector encoding for a selected UniCAR. The lentiviral vector is pLVX-EF1alpha UniCAR 28/ζ (Clontech, Takara Bio Group) as shown in FIG. 3, in which the lentiviral parts of the vector are derived from the human immunodeficiency virus (HIV) and the MSC/IRES/ZxGreenI portion was replaced by the UniCAR construct.

Figure 4:
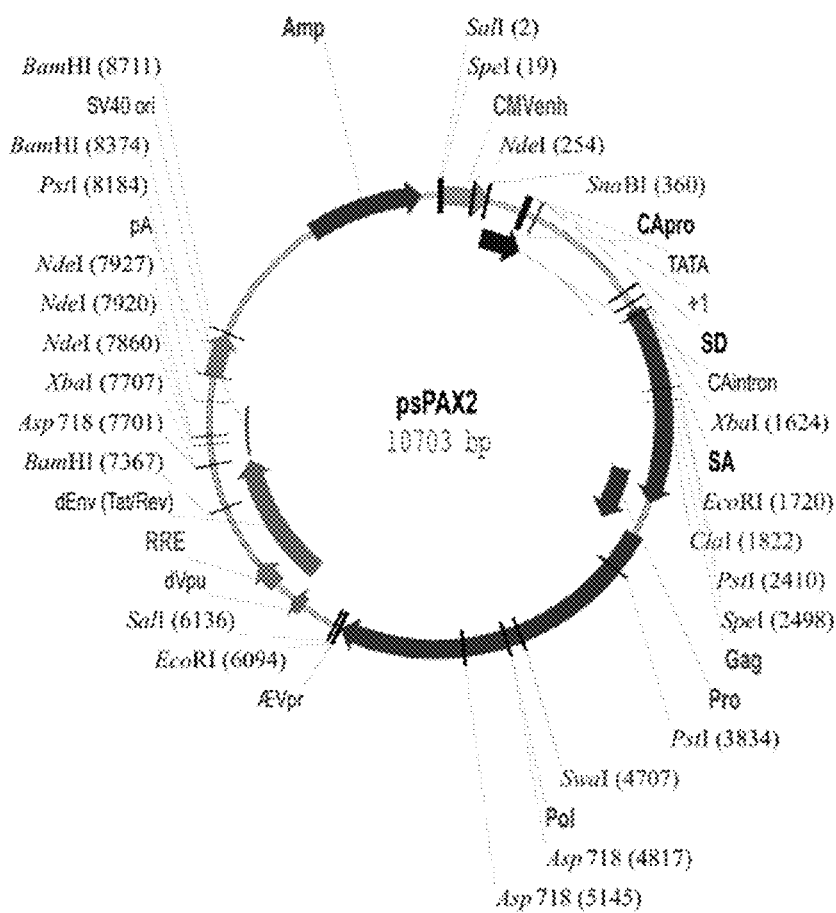
FIG. 4 shows the group specific antigen (gag) and Polymerase (pol) encoding plasmid psPAX2 with CMV enhancer and promoter (CMVenh), splice donor (SD), splice acceptor (SA), Group-specific antigen (Gag), Precursor protein encoding the protease protein (Pro), Protein encoding the reverse transcriptase and integrase (Pol), rev responsive element (RRE), ampicillin (Amp).
Figure 5:
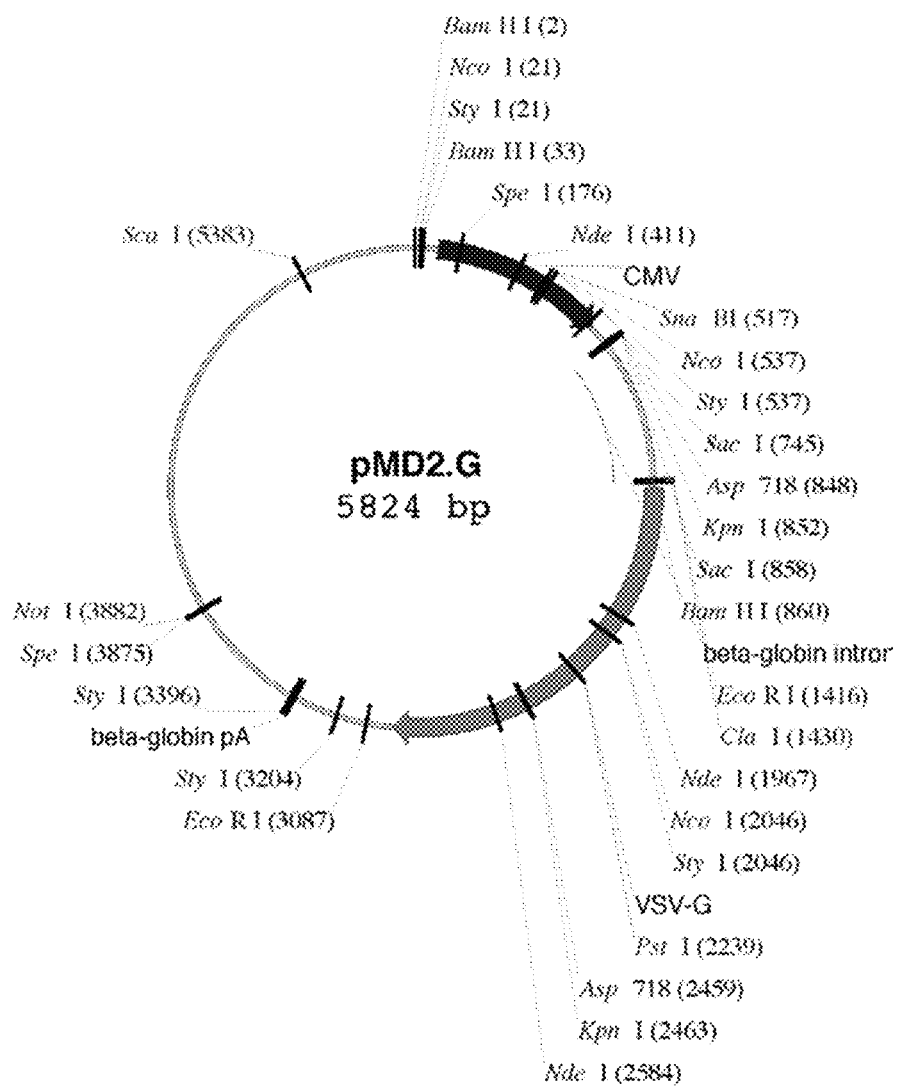
FIG. 5 shows the plasmid pMD2.G encoding for an envelope with CMV enhancer and promoter (CMV), beta-globin intron (beta-globin intror), beta-globin poly adenosine tail (beta-globin pA).

The lentiviral particles are produced by transient transfection of human embryonal kidney (HEK) 293T (ACC 635) cells with the UniCAR encoding lentiviral vector plasmid and cotransfection with a group specific antigen (gag) and Polymerase (pol) encoding plasmid (psPAX2) as depicted in FIG. 4 plus a plasmid encoding for an envelope (pMD2.G) as shown in FIG. 5. After transfection, the packaging plasmid expresses Gag and Pol protein of HIV-1. The plasmid MD2.G encodes the glycoprotein of the vesicular stomatitis virus (VSV-G). VSV-G protein is used to lentiviral vectors to transduce a broad range of mammalian cells. Various envelopes from different virus species can be utilized for this purpose. Lentiviral vectors can successfully pseudotype with the envelope glycoproteins (Env) of amphotropic murine leukemia virus (MLV) or the G protein of vesicular stomatitis virus (VSV-G), a modified envelope of the prototypic foamy virus (PFV) or chimeric envelope glycoprotein variants derived from gibbon ape leukemia virus (GaLV) and MLV.

Supernatants from transfected HEK293T cells are harvested 24 h to 96 h after transfection and virus particles are concentrated from the supernatant by ultracentrifugation or other methods. For lentiviral transduction of immune cells peripheral blood mononuclear cells (PBMC) or isolated T cells are activated with mab specific for the CD3 complex, e.g. clone OKT3 or UCHT1, either given in solution or coated to plastic cell culture dishes or magnetic beads. Activation of PBMC or isolated T cells is further enhanced by stimulating costimulatory pathways with mabs or ligands specific for CD27, CD28, CD134 or CD137 either alone or in combinations and the supply with exogenous recombinant cytokines like interleukin (IL)-2, IL-7, IL-12, IL-15 and IL-21. Concentrated or non-concentrated virus particles are added to PBMC or T cell cultures 24 h to 96 h after initial administration of activating CD3 antibodies and/or recombinant cytokines as single or multiple doses.

Stable transduction of T cells may be determined flow cytometry after staining with tag-containing targeting modules for surface expression of UniCARs or mabs directed against the fourth domain of UniCARs from day 3 onwards after final administration of virus supernatant. UniCAR transduced T cells can be propagated in vitro by culturing them under supply of recombinant cytokines and activating anti-CD3 mabs.

In case the UniCAR harbors the optional fourth domain, a peptide sequence forming a linear epitope for a mab, immune cells genetically modified to express UniCARs can be specifically propagated in vitro by coating a mab or antibody fragments thereof binding to the fourth UniCAR domain to the surface of culture dishes or to beads of any kind, which are added to the cell culture at a defined ratio of 1 bead to 1 to 4 UniCAR engrafted effector cells. The binding of surface-coated mabs to the UniCAR peptide domain induces cross-linkage of cell-surface expressed UniCARs and formation of an immune synapse, which leads to the activation of signal pathways specifically triggered by the signal domain of the UniCAR. Depending on the signal pathways induced, this may lead to enhance proliferation and sustained resistance against activation-induced cell death of the UniCAR carrying immune cells and therefore enrichment of UniCAR genetically modified immune cells in a mixed population.

The optional fourth domain, a peptide sequence forming a linear epitope for a mab, can be further utilized to enrich and purify UniCAR expressing immune cells from mixed populations. Enrichment and purification is performed with the help of a mab or antibody fragment thereof binding to the fourth UniCAR domain to either mark UniCAR expressing cells for cell sorting or to transiently link the UniCAR expressing immune cell to small particles, which can be utilized for cell isolation. In one aspect, UniCAR engrafted immune cells are incubated with the mab recognizing the fourth domain. Next, magnetic beads are added, which are conjugated with antibodies or fragments thereof directed against the species- and isotype specific heavy and light chains of the mab binding to the optional fourth domain. Thus, UniCAR expressing immune cells and magnetic beads are linked and are trapped and separated from other immune cells in a magnetic field.

The present invention further comprises a pharmaceutical composition comprising a kit according to the invention.

The pharmaceutical compositions are preferably administered parenterally, particularly preferred intravenously. In an embodiment, the pharmaceutical composition is present in a form suitable for intravenous administration. Preferably, the pharmaceutical composition is a solution, emulsion, or suspension.

In an embodiment, the pharmaceutical composition is an injectable buffered solution comprising between 0.1 µg/ml to 50 mg/ml of the targeting module, preferably between 0.5 µg/ml to 5 mg/ml of the targeting module.

In an embodiment, the pharmaceutical composition further comprises a pharmaceutically acceptable dilution agent or carrier. In an embodiment the carrier is water, buffered water, 0.4% saline solution, 0.3% glycine or a similar solvent. In an embodiment, the buffered water is selected from histidine buffered water at a pH value of pH 5.0 to pH 7.0, especially preferred at a pH of pH 6.0; or sodium succinate, sodium citrate, sodium phosphate, or potassium phosphate buffered water. In an embodiment, the buffer has a concentration of 1 mmol/l (mM) to 500 mM, preferably 1 mM to 50 mM, especially preferred 5 mM to 10 mM. In an embodiment, the carrier comprises sodium chloride, preferably in a concentration between 0 mM to 300 mM, especially preferred 150 mM. In an embodiment, the pharmaceutical composition further comprises a stabilizer, preferably in a concentration between 1 mM to 50 mM, especially preferred between 5 mM and 10 mM. In an embodiment, the stabilizer is L-methionine.

In an embodiment, the pharmaceutical composition further comprises pharmaceutically acceptable excipients. The term "pharmaceutically acceptable excipients" refers to compounds which provide approximately physiological conditions and/or to increase the stability, such as agents for adjusting the pH value and buffering agents, agents for adjusting the toxicity and the like. In an embodiment, pharmaceutically acceptable excipients are selected from sodium acetate, sodium chloride, potassium chloride, calcium chloride and sodium lactate.

In a preferred embodiment, the pharmaceutical composition comprises the targeting module in a dosage quantity of 0.1 µg/kg to 1 mg/kg per administration, preferably dosage quantities of 1 µg/kg to 100 µg/kg of body weight.

In a further embodiment, the pharmaceutical composition is sterile. The pharmaceutical composition is sterilized by conventional well-known techniques.

In an embodiment, the pharmaceutical composition comprising a kit according to the invention is used for administration to a subject.

The invention further comprises a kit according to the invention or a pharmaceutical composition according to the invention for use in the treatment of cancer, infections and autoimmune disorders. The term "autoimmune disorder" refers to an abnormal immune response of the body against substances and tissues normally present in the body (autoimmunity).

In an embodiment, the kit according to the invention or a pharmaceutical composition according to the invention is used for preparing a medication for therapeutic and/or diagnostic use in case of cancer or an autoimmune disease.

The invention also encompasses a method for treatment of a human having cancer or an autoimmune or inflammatory disease by administration of a kit according to the invention or a pharmaceutical composition according to the invention. For therapeutic applications, a sterile kit according to the invention or a pharmaceutical composition according to the invention, comprising a pharmacologically effective quantity of targeting module according to the invention and a vector or a cell comprising a nucleic acid encoding a universal chimeric antigen receptor, is administered to a patient in order to treat the aforementioned illnesses.

In an embodiment, the kit according to the invention or the pharmaceutical composition according to the invention is used for stimulating a universal chimeric antigen receptor mediated immune response in a mammal.

A method for stimulating a universal chimeric antigen receptor mediated immune response in a mammal, the method comprising:
 administering to a mammal an effective amount of a vector or a cell comprising a nucleic acid encoding a universal chimeric antigen receptor, wherein the universal chimeric antigen receptor comprises three domains, wherein the first domain is a tag-binding domain, the second domain is an extracellular hinge and a transmembrane domain and the third domain is a signal transduction domain, wherein tag-binding domain binds to a tag from a human nuclear protein
 administering a targeting module according to the invention,
 wherein the targeting modules are administered to a subject prior to, or concurrent with, or after administration of the universal chimeric antigen receptor-expressing effector cells.

In a preferred embodiment, the kit according to the invention, in particular the targeting module and vector or cell, or the pharmaceutical composition according to the invention are administered to humans.

In further embodiments, the recently described embodiments can be combined.

CITED NON-PATENT LITERATURE

Afshar-Oromieh A, Avtzi E, Giesel F L, Holland-Letz T, Linhart H G, Eder M, Eisenhut M, Boxler S, Hadaschik B A, Kratochwil C, Weichert W, Kopka K, Debus J, Haberkorn U (2015) The diagnostic value of PET/CT imaging with the (68)Ga-labelled PSMA ligand HBED-CC in the diagnosis of recurrent prostate cancer. Eur J Nucl Med Mol Imaging. 42(2): 197-209.

Arap M A, Lahdenranta J, Mintz P J, Hajitou A, Sarkis A S, Arap W, Pasqualini R (2004) Cell surface expression of the stress response chaperone GRP78 enables tumor targeting by circulating ligands. Cancer Cell 6 (3): 275-284.

Arap W, Pasqualini R, Ruoslahti E (1998) Cancer treatment by targeted drug delivery to tumor vasculature in a mouse model. Science 279: 377-380.

Barrett J A, Coleman R E, Goldsmith S J, Vallabhajosula S, Petry N A, Cho S, Armor T, Stubbs J B, Maresca K P, Stabin M G, Joyal J L, Eckelman W C, Babich J W (2013) First-in-man evaluation of 2 high-affinity PSMA-avid small molecules for imaging prostate cancer. J Nucl Med. 54: 380-387.

Beaujouan J C, Torrens Y, Saffroy M, Kemel M-L, Glowinski J (2004) A 25 year adventure in the field of tachykinins. Peptides 25: 339-357.

Brady L W, Heilmann H-P, Molls M, Nieder C, Ed. Baum R P (2014) Therapeutic Nuclear Medicine. Springer. DOI 10.1007/978-3-540-36719-2.

Broda E, Mickler F M, Lachelt U, Morys S, Wagner E, Brachle C (2015) Assessing potential peptide targeting ligands by quantification of cellular adhesion of model nanoparticles under flow conditions. J Control Release 10: 79-85.

Brom M, Oyen W J, Joosten L, Gotthardt M, Boerman O C (2010) $^{68}$Ga-labelled exendin-3, a new agent for the detection of insulinomas with PET. Eur J Nucl Med Mol Imaging 37: 1345-1355.

Buchegger F, Bonvin F, Kosinski M, Schaffland A O, Prior J, Reubi J C, Blauenstein P, Tourwe D, Garcia Garayoa E, Bischof Delaloye A (2003) Radiolabeled neurotensin analog, $^{99m}$Tc-NT-XI, evaluated in ductal pancreatic adenocarcinoma patients. J Nucl Med 44: 1649-1654.

Burg M A, Pasqualini R, Arap W, Ruoslahti E, Stallcup W B (1999) NG2 proteoglycan-binding peptides target tumor neovasculature. Cancer Res. 59: 2869-2874.

Cardó-Vila M, Arap W, Pasqualini R (2003) Alpha v beta 5 integrin-dependent programmed cell death triggered by a peptide mimic of annexin V. Mol Cell. 11(5): 1151-1162.

Cardó-Vila M, Zurita A J, Giordano R J, Sun J, Rangel R, Guzman-Rojas L, Anobom C D, Valente A P, Almeida F C, Lahdenranta J, Kolonin M G, Arap W, Pasqualini R (2008) A ligand peptide motif selected from a cancer patient is a receptor-interacting site within human interleukin-11. PLoS One. 3, e3452.

Cardó-Vila M, Giordano R J, Sidman R L, Bronk L F, Fan Z, Mendelsohn J, Arap W, Pasqualini R (2010) From combinatorial peptide selection to drug prototype (II): targeting the epidermal growth factor receptor pathway. Proc. Natl. Acad. Sci. 107: 5118-5123.

Carpenito C, Milone M C, Hassan R, Simonet J C, Lakhal M, Suhoski, M M, Varela-Rohena A, Haines K M, Heitjan D, Albelda S M, Carrol R G, Riley J L, Pastan, I, June C H (2009) Control of large, established tumor xenografts with genetically retargeted human T cells containing CD28 and CD137 domains. Proc Natl Acad Sci USA. 106 (9): 3360-3365.

Cartellieri M, Bachmann M, Feldmann A, Bippes C, Stamova S, Wehner R, Temme A, Schmitz M (2010) Chimeric antigen receptor-engineered T cells for immunotherapy of cancer. J Biomed Biotechnol. doi: 10.1155/2010/956304.

Cartellieri M, Feldmann A, Koristka S, Arndt, Loff S, Ehninger A, von Bonin M, Bejestani E P, Ehninger G, Bachmann M P (2016) Switching CAR T cells on and off: a novel modular platform for retargeting of T cells to AML blasts. Blood Cancer J.: 6 (8): e458.

Cartellieri M, Koristka S, Arndt C, Feldmann A, Stamova S, von Bonin M, Topfer K, Kruger T, Geib M, Michalk I, Temme A, Bornhauser M, Lindemann D, Ehninger G, Bachmann M P (2014) A novel ex vivo isolation and expansion procedure for chimeric antigen receptor engrafted human T cells. PLOS One. 9 (4): e93745.

Chen J, Cheng Z, Miao Y, Jurisson S S, Quinn T P (2002) α-melanocyte-stimulating hormone peptide analogs labeled with technetium-99m and indium-111 for malignant melanoma targeting. Cancer 94 (4): 1196-1201.

Clark-Lewis I, Schumacher C, Baggiolini M, Moser B (1991) Structure-activity relationships of interleukin-8 determined using chemically synthesized analogs. Critical role of $NH_2$-terminal residues and evidence for uncoupling of neutrophil chemotaxis, exocytosis, and receptor binding activities. The JBC 266: 23128-23134.

De Rosa L, Finetti F, Diana D, Di Stasi R, Auriemma S, Romanelli A, Fattorusso R, Ziche M, Morbidelli L, D'Andrea L D (2016) Miniaturizing VEGF: Peptides mimicking the discontinuous VEGF receptor-binding site modulate the angiogenic response. Scientific Reports 6, 31295.

de Visser M, Janssen P J, Srinivasan A, Reubi J C, Waser B, Erion J L, Schmidt M A, Krenning E P, de Jong M (2003) Stabilised $^{111}$In-labelled DTPA- and DOTA-conjugated neurotensin analogues for imaging and therapy of exocrine pancreatic cancer. Eur J Nucl Med Mol Imaging 30: 1134-1139.

Decristoforo C, Hernandez Gonzalez I, Carlsen J, Rupprich M, Huisman M, Virgolini I, Wester H-J, Haubner R (2008) $^{68}$Ga- and $^{111}$In-labelled DOTA-RGD peptides for imaging of avβ3 integrin expression. Eur J Nucl Med Mol Imaging 35: 1507-1515.

Dumont R A, Deininger F, Haubner R, Maecke H R, Weber W A, Fani M (2011) Novel $^{64}$Cu- and $^{68}$Ga-labeled RGD conjugates show improved PET imaging of $a_v\beta_3$ integrin expression and facile radiosynthesis. J Nucl Med 52: 1276-1284.

Frigault M J, Lee J, Basil M C, Carpenito C, Motohashi S, Scholler J, Kawalekar O U, Guedan S, McGettigan S E, Posey A D Jr, Ang S, Cooper L J, Platt J M, Johnson F B, Paulos C M, Zhao Y, Kalos M, Milone M C, June C H (2015) Identification of chimeric antigen receptors that mediate constitutive or inducible proliferation of T cells. Cancer Immunol Res. 3 (4): 356-367.

Fedorov V D, Themeli M, Sadelain M (2013) PD-1- and CTLA-4-based inhibitory chimeric antigen receptors (iCARs) divert off-target immunotherapy responses. Sci Transl Med. 5 (215): 215ra172.

Finney H M, Akbar A N, Lawson A D (2004) Activation of resting human primary T cells with chimeric receptors: costimulation from CD28, inducible costimulator, CD134, and CD137 in series with signals from the TCR zeta chain. J Immunol. 172 (1): 104-113.

Froberg A C, de Jong M, Nock B A, Breeman W A P, Erion J L, Maina T, Verdijsseldonck M, de Herder W W, van der Lugt A, Kooij P P M, Krenning E P (2009) Comparison of three radiolabelled peptide analogues for CCK-2 receptor scintigraphy in medullary thyroid carcinoma. Eur J Nucl Med Mol Imaging 36: 1265-1272.

Gade T P, Hassen W, Santos E, Gunset G, Saudemont A, Gong M C, Brentjens R, Zhong X S, Stephan M, Stefanski J, Lyddane C, Osborne J R, Buchanan I M, Hall S J, Heston W D, Rivière I, Larson S M, Koutcher J A, Sadelain M (2005) Targeted elimination of prostate cancer by genetically directed human T lymphocytes. Cancer Res. 65 (19): 9080-9088.

Gong M C, Latouche J B, Krause A, Heston W D W, Bander N H, Sadelain M (1999) Cancer patient T cells genetically targeted to prostate-specific membrane antigen specifically lyse prostate cancer cells and release cytokines in response to prostate-specific membrane antigen. Neoplasia. 1 (2): 123-127.

Gonzalez N, Moody T W, Igarashi H, Ito T, Jensen R T (2008) Bombesin-related peptides and their receptors: recent advances in their role in physiology and disease states. Curr Opin Endocrinol Diabetes Obes 15: 58-64.

Grupp S A, Kalos M, Barrett D, Aplenc R, Porter D L, Rheingold S R, Teachey D T, Chew A, Hauck B, Wright F, Milone M C, Levine B L, June C H (2013) Chimeric Antigen Receptor-Modified T Cells for Acute Lymphoid Leukemia. N Engl J Med. 368, 1509-1518.

Hanaoka H, Mukai T, Tamamura H, Mori T, Ishino S, Ogawa K, Iida Y, Doi R, Fujii N, Saji H (2006) Development of a $^{111}$In-labeled peptide derivative targeting a chemokine receptor, CXCR4, for imaging tumors. Nucl Med Biol. 33: 489-494.

Haubner R, Weber W A, Beer A J, Vabuliene E, Reim D, Sarbia M, Becker K-F, Goebel M, Hein R, Wester H-J, Kessler H, Schwaiger M (2005) Noninvasive visualization of the activated avβ3 integrin in cancer patients by positron emission tomography and [$^{18}$F]Galacto-RGD. PLOS Med 2: e70.

Hessenius C, Bader M, Meinhold H, Bohmig M, Faiss S, Reubi J-C, Wiedenmann B (2000) Vasoactive intestinal peptide receptor scintigraphy in patients with pancreatic adenocarcinomas or neuroendocrine tumours. Eur J Nucl Med 27: 1684-1693.

Hombach A, Sent D, Schneider C, Heuser C, Koch D, Pohl C, Seliger B, Abken H (2001) T-cell activation by recombinant receptors: CD28 costimulation is required for interleukin 2 secretion and receptor-mediated T-cell proliferation but does not affect receptor-mediated target cell lysis. Cancer Res. 61 (5): 1976-1982.

Hombach A A, Kofler D, Hombach A, Rappl G, Abken H (2007) Effective proliferation of human regulatory T cells requires a strong costimulatory CD28 signal that cannot be substituted by IL-2. J Immunol. 179 (11): 7924-7931.

Hombach A A, Abken H (2011) Costimulation by chimeric antigen receptors revisited the T cell antitumor response benefits from combined CD28-OX40 signalling. Int J Cancer. 129 (12): 2935-2944.

Hombach A A, Abken H (2013) Of chimeric antigen receptors and antibodies: OX40 and 41BB costimulation sharpen up T cell-based immunotherapy of cancer. Immunotherapy. 5 (7): 677-681.

Iwasaki K, Goto Y, Katho T, Yamashita T, Kaneko S, Suga H (2015) A Fluorescent Imaging Probe Based on a Macrocyclic Scaffold That Binds to Cellular EpCAM. J Mol Evol. 81 (5-6): 210-217.

Jacobson O, Weiss I D, Kiesewetter D O, Farber J M, Chen X (2010) PET of tumor CXCR4 expression with 4-$^{18}$F-T140. J Nucl Med. 51: 1796-1804.

Kajiwara K, Saito A, Ogata S, Tanihara M (2004) Synthetic peptides corresponding to ligand-binding region of death receptors, DR5, Fas, and TNFR, specifically inhibit cell death mediated by the death ligands, respectively. Biochim Biophysica Acta—Proteins and Proteomics. 1699 (1-2): 131-137.

Kaltsas G A, Papadogias D, Makras P, Grossman A B (2005) Treatment of advanced neuroendocrine tumours with radiolabelled somatostatin analogues. Endocr Relat Cancer 12: 683-699.

Karjalainen K, Jaalouk D E, Bueso-Ramos C E, Zurita A J, Kuniyasu A, Eckhardt B L, Marini F C, Lichtiger B, O'Brien S, Kantarjian H M, Cortes J E, Koivunen E, Arap W, Pasqualini R (2011) Targeting neuropilin-1 in human leukemia and lymphoma. Blood. 117: 920-927M.

Kershaw M H, Westwood J A, Parker L L, et al. (2006) A phase I study on adoptive immunotherapy using gene-modified T cells for ovarian cancer. Clin Cancer Res. 12 (20): 6106-15.

Kolenc-Peitl P, Mansi R, Tamma M, Gmeiner-Stopa T, Sollner-Dolenc M, Waser B, Baum R P, Reubi, J C, Maecke H R (2011) Highly improved metabolic stability and pharmacokinetics of indium-111-DOTA-gastrin conjugates for targeting of the gastrin receptor. J Med Chem 54: 2602-2609.

Kolonin M G, Bover L, Sun J, Zurita A J, Do K A, Lahdenranta J, Cardó-Vila M, Giordano R J, Jaalouk D E, Ozawa M G, Moya C A, Souza G R, Staquicini F J, Kunyiasu A, Scudiero D A, Holbeck S L, Sausville E A, Arap W, Pasqualini R (2006) Ligand-directed surface profiling of human cancer cells with combinatorial peptide libraries. Cancer Res. 66: 34-40.

Lamers C H, Sleijfer S, Willemsen R A, Debets R, Kruit WHJ, Gratama J W, Stoter G (2004) Adoptive immuno-gene therapy of cancer with single chain antibody [scFv (Ig)] gene modified T lymphocytes. J Biol Regul Homeost Agents. 18 (2): 134-140.

Lamers C H, Sleijfer S, Vulto A G, Kruit W H, Kliffen M, Debets R, Gratama J W, Stoter G, Oosterwijk E. (2006) Treatment of metastatic renal cell carcinoma with autologous T-lymphocytes genetically retargeted against carbonic anhydrase IX: first clinical experience. J Clin Oncol. 24, e20-e22.

Laverman P, Sosabowski J K, Boerman O C, Oyen W J G (2012) Transforming growth factor beta receptor as example fur surface-expressed serine/threonine kinase receptors: Radiolabelled peptides for oncological diagnosis. Eur J Nucl Med Mol Imaging 39 (Suppl 1): 78-92.

Maher J, Brentjens R J, Gunset G, Riviere I, Sadelain M (2002) Human T-lymphocyte cytotoxicity and proliferation directed by a single chimeric TCRzeta/CD28 receptor. Nat Biotechnol. 20 (1): 70-75.

Marchió S, Lahdenranta J, Schlingemann R O, Valdembri D, Wesseling P, Arap M A, Hajitou A, Ozawa M G, Trepel M, Giordano R J, Nanus D M, Dijkman H B, Oosterwijk E, Sidman R L, Cooper M D, Bussolino F, Pasqualini R, Arap W (2004) Aminopeptidase A is a functional target in angiogenic blood vessels. Cancer Cell. 5: 151-162.

Merlo A, Hausmann O, Wasner M et al (1999) Locoregional regulatory peptide receptor targeting with the diffusible somatostatin analogue $^{90}$Y-labeled DOTA$^0$-D-Phe$^1$-Tyr$^3$-octreotide (DOTATOC): a pilot study in human gliomas. Clin Cancer Res 5, 1025-1033.

Michaloski J S, Redondo A R, Magalhaes L S, Cambui C C, Giordano R J (2016) Discovery of pan-VEGF inhibitory peptides directed to the extracellular ligand-binding domains of the VEGF receptors. Sci Adv. 2(10): e1600611.

Milone M C, Fish J D, Carpenito C, Carroll R G, Binder G K, Teachey D, Samanta M, Lakhal M, Gloss B, Danet-Desnoyers G, Campana D, Riley J L, Grupp S A, June C H (2009) Chimeric receptors containing CD137 signal transduction domains mediate enhanced survival of T cells and increased antileukemic efficacy in vivo. Mol Ther. 17 (8): 1453-1464.

Morgan R A, Yang J C, Kitano M, Dudley M E, Laurencot C M, Rosenberg S A (2010) Case report of a serious adverse event following the administration of T cells transduced with a chimeric antigen receptor recognizing ERBB2. Mol Ther. 18, 843-851.

Nagy A, Schally A V (2005) Targeting of cytotoxic luteinizing hormone-releasing hormone analogs to breast, ovarian, endometrial, and prostate cancers. Biol. Reprod. 73 (5): 891-859.

Ohki-Hamazaki H, Iwabuchi M, Maekawa F (2005) Development and function of bombesin-like peptides and their receptors. Int J Dev Biol. 49: 293-300.

Pasqualini R, Koivunen E, Kain R, Lahdenranta J, Sakamoto M, Stryhn A, Ashmun R A, Shapiro L H, Arap W, Ruoslahti E (2000) Aminopeptidase N is a receptor for tumor-homing peptides and a target for inhibiting angiogenesis. Cancer Res. 60: 722-727.

Pinthus J H, Waks T, Kaufman-Francis K, Schindler D G, Harmelin A, Kanety H, Ramon J, Eshhar Z (2003) Immuno-gene therapy of established prostate tumors using chimeric receptor-redirected human lymphocytes. Cancer Res. 63 (10): 2470-6.

Pinthus J H, Waks T, Malina V, Kaufman-Francis K, Harmelin A, Aizenberg I, Kanety H, Ramon J, Eshhar Z (2004) Adoptive immunotherapy of prostate cancer bone lesions using redirected effector lymphocytes. J Clin Invest. 114 (12): 1774-81.

Popovics P, Schally A V, Szalontay L, Block N L, Rick F G (2014) Targeted cytotoxic analog of luteinizing hormone-releasing hormone (LHRH), AEZS-108 (AN-152), inhibits the growth of DU-145 human castration-resistant prostate cancer in vivo and in vitro through elevating p21 and ROS levels. Oncotarget 5 (12): 4567-4578.

Raderer M, Kurtaran A, Leimer M, Angelberger P, Niederle B, Vierhapper H., Vorbeck F, Hejna MHL, Scheithauer W., Pidlich J., Virgolini I (2000) Value of peptide receptor scintigraphy using $^{123}$I-vasoactive intestinal peptide and $^{111}$In-DTPA-D-Phe1-octreotide in 194 carcinoid patients: Vienna University Experience, 1993 to 1998. J Clin Oncol 18: 1331-1336.

Reubi J C, Gugger M, Waser B, Schaer J-C(2001) Ye-mediated effect of neuropeptide Y in cancer: breast carcinomas as targets. Cancer Res. 61: 4636-4641.

Sai K K S, Sattiraju A, Almaguel F G, Xuan A, Rideout S, Krishnaswamy R S, Zhang J, Herpai D M, Debinski W, Mintz A (2017) Peptide-based PET imaging of the tumor restricted IL13RA2 biomarker. Oncotarget 8 (31): 50997-51007

Soudy R, Etayash H, Bahadorani K, Lavasanifar A, Kaur K (2017) Breast Cancer Targeting Peptide Binds Keratin 1: A New Molecular Marker for Targeted Drug Delivery to Breast Cancer. Molecular Pharmaceutics 14 (3): 593-604.

Staquicini F I, Tandle A, Libutti S K, Sun J, Zigler M, Bar-Eli M, Aliperti F, Perez E C, Gershenwald J E, Mariano M, Pasqualini R, Arap W, Lopes J D (2008) A subset of host B lymphocytes controls melanoma metastasis through a melanoma cell adhesion molecule/MUC18-dependent interaction: evidence from mice and humans. Cancer Res. 68(20): 8419-8428.

Staquicini F I, Qian M D, Salameh A, Dobroff A S, Edwards J K, Cimino D F, Moeller B F, Kelly B, Nunez M I, Tang X, Liu D D, Lee J J, Hong W K, Ferrara F, Bradbury A R, Lobb R R, Edelman M J, Sidman R L, Wistuba I I, Arap W, Pasqualini R (2015) Receptor tyrosine kinase EphA5 is a functional molecular target in human lung cancer. J. Biol. Chem. 290: 7345-7359.

Topfer K, Cartellieri M, Michen S, Wiedemuth R, Müller N, Lindemann D, Bachmann M, Fussel M, Schackert G, Temme A (2015) DAP12-based activating chimeric antigen receptor for N K cell tumor immunotherapy. J Immunol. 194 (7): 3201-3212.

Vallabhajosula S, Nikolopoulou A, Babich J W, Osborne J R, Tagawa S T, Lipai I, Solnes L, Maresca K P, Armor T, Joyal J L, Crummet R, Stubbs J B, Goldsmith S J (2014) $^{99m}$Tc-labeled small-molecule inhibitors of prostate-specific membrane antigen: pharmacokinetics and biodistribution studies in healthy subjects and patients with metastatic prostate cancer. J Nucl Med. 55: 1791-1798.

Vidal C I, Mintz P J, Lu K, Ellis L M, Manenti L, Giavazzi R, Gershenson D M, Broaddus R, Liu J, Arap W, Pasqualini R (2004) An HSP90-mimic peptide revealed by fingerprinting the pool of antibodies from ovarian cancer patients. Oncogene. 23: 8859-8867.

Wang X-F, Birringer M, Dong L-F, Veprek P, Low P, Swettenham E, Stantic M, Yuan L-H, Zobalova R, Wu K, Ledvina M, Ralph S J, Neuzil J (2007a) A Peptide Conjugate of Vitamin E Succinate Targets Breast Cancer Cells with High ErbB2 Expression. Cancer Res. 67 (7): 3337-3344.

Wang J, Jensen M, Lin Y, Sui X, Chen E, Lindgren C G, Till B, Raubitschek A, Forman S J, Qian X, James S, Greenberg P, Riddell S, Press O W (2007b) Optimizing adoptive polyclonal T cell immunotherapy of lymphomas, using a chimeric T cell receptor possessing CD28 and CD137 costimulatory domains. Hum Gene Ther. 18 (8): 712-725.

Wild D, Behe M, Wicki A, Storch D, Waser B, Gotthardt M, Keil B, Christofori G, Reubi J C, Macke H R (2006) [Lys$^{40}$(Ahx-DTPA-$^{111}$In)NH$_2$]exendin-4, a very promising ligand for glucagon-like peptide-1 (GLP-1) receptor targeting. J Nucl Med 47: 2025-2033.

Wild D, Wicki A, Mansi R, Behe M, Keil B, Bernhardt P, Christofori G, Ell P J, Macke H R (2010) Exendin-4-based radiopharmaceuticals for glucagon like peptide-1 receptor PET/C T and SPECT/C T. J Nucl Med 51: 1059-1067.

Wild D, Fani M, Behe M et al (2011) First clinical evidence that imaging with somatostatin receptor antagonists is feasible. J Nucl Med 52: 1412-1417.

Yang J, Guo H, Gallazzi F, Berwick M, Padilla R S, Miao Y (2009) Evaluation of A Novel Arg-Gly-Asp-Conjugated Alpha-Melanocyte Stimulating Hormone Hybrid Peptide for Potential Melanoma Therapy. Bioconjug Chem. 20 (8): 1634-1642.

Zhang T, Lemoi B A, Sentman C L (2005) Chimeric NK-receptor-bearing T cells mediate antitumor immunotherapy. Blood. 106 (5): 1544-1551.

Zhang T, Barber A, Sentman C L (2006) Generation of antitumor responses by genetic modification of primary human T cells with a chimeric NKG2D receptor. Cancer Res. 66 (11): 5927-5933.

Zhao Y, Wang Q J, Yang S, Kochenderfer J N, Zheng Z, Zhong X, Sadelain M, Eshhar Z, Rosenberg S A, Morgan R A (2009) A herceptin-based chimeric antigen receptor with modified signaling domains leads to enhanced survival of transduced T lymphocytes and antitumor activity. J Immunol. 183 (9): 5563-5574.

REFERENCE SIGNS 1 first domain, a tag-binding domain.
2 second domain, an extracellular hinge and a transmembrane domain.
3 third domain, a signal transduction domain.
4 optional fourth domain, a short peptide linker.

The invention claimed is:

1. A targeting module comprising:
   a glutamate-urea-lysine motif,
   a chelator, and
   a tag, wherein the tag comprises a human nuclear La protein epitope selected from SEQ ID NOs: 25 and 27.

2. The targeting module according to claim 1, selected from

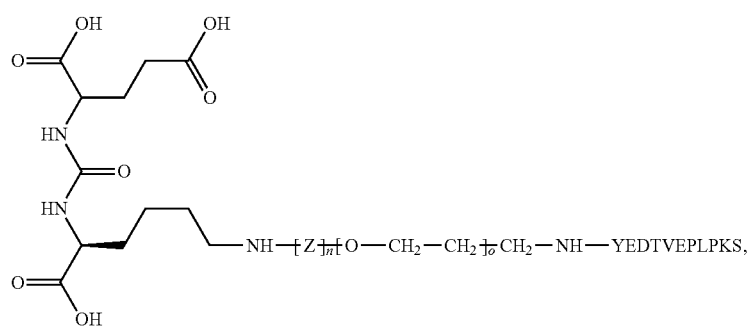

(Formula I)

which contains SEQ ID NO: 28, and

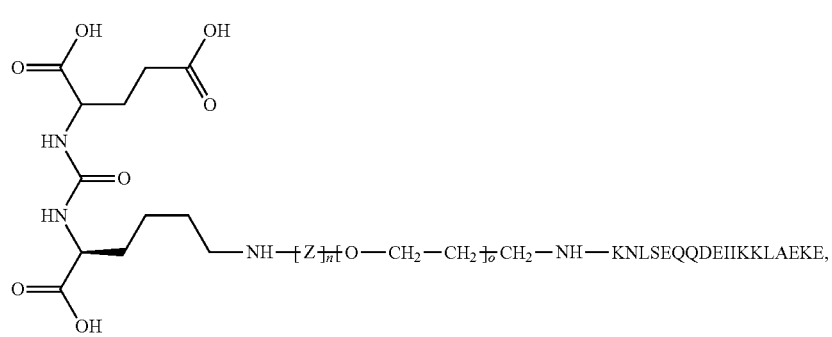

(Formula II)

which contains SEQ ID NO: 27,
wherein Z is a chelator
n is an integer
is 2 or more.

3. A pharmaceutical composition comprising a targeting module according to claim 1.

4. A method for the treatment of a prostate specific membrane antigen expressing cancer comprising administering to a patient the targeting module according to claim 1 and a vector or a cell comprising a nucleic acid encoding a universal chimeric antigen receptor that comprises:
  a tag-binding domain comprising
    a variable region heavy chain comprising SEQ ID NO: 21 and a variable region light chain comprising SEQ ID NO: 22, or
    a variable region heavy chain comprising SEQ ID NO: 23 and a variable region light chain comprising SEQ ID NO: 24;
  an extracellular hinge and a transmembrane domain; and
  a signal transduction domain.

5. The method of claim 4, wherein the targeting module has a structure selected from

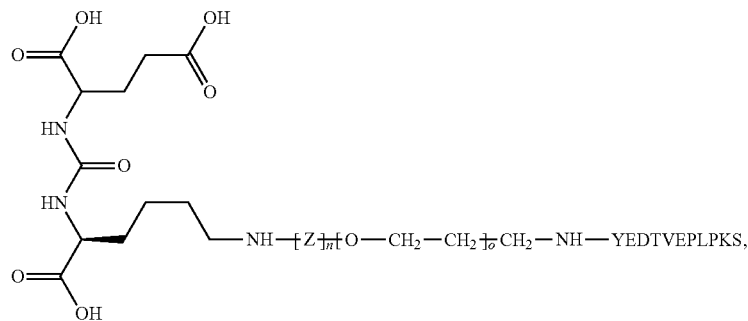
(Formula I)

which contains SEQ ID NO: 25, and

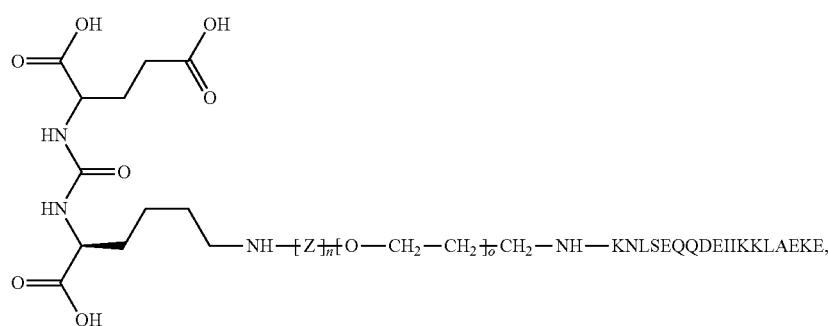
(Formula II)

which contains SEQ ID NO: 27
wherein Z is a chelator
n is an integer
is 2 or more.

6. The method of claim 4, wherein the extracellular hinge and transmembrane domain is selected from hinge and transmembrane domains of human CD28 molecule, CD8a chain NK cell receptors, parts of the constant region of an antibody, and combinations thereof.

7. The method of claim 4, wherein the signal transduction domain is selected from the group consisting of cytoplasmic regions of CD28, CD137 (4-1BB), CD134 (OX40), DAP10 and CD27, programmed cell death-1 (PD-1), cytotoxic T-lymphocyte antigen 4 (CTLA-4), cytoplasmic regions of CD3 chains, DAP12, and activating Fc receptors.

8. The method of claim 4, wherein the nucleic acid comprises a nucleotide sequence according to SEQ ID NO: 1, 9, 13 or 16 encoding for a universal chimeric antigen receptor with an amino acid sequence according to SEQ ID NO: 17, 18, 19, or 20.

9. A kit comprising
a) a targeting module according to claim 1 and
b) a vector or a cell comprising a nucleic acid encoding a universal chimeric antigen receptor that comprises:
  a tag-binding domain comprising
    a variable region heavy chain comprising SEQ ID NO: 21 and a variable region light chain comprising SEQ ID NO: 22, or
    a variable region heavy chain comprising SEQ ID NO: 23 and a variable region light chain comprising SEQ ID NO: 24;
  an extracellular hinge and a transmembrane domain; and
  a signal transduction domain.

10. The kit according to claim 9, wherein the extracellular hinge and transmembrane domain is selected from hinge and transmembrane domains of human CD28 molecule, CD8a chain NK cell receptors parts of the constant region of an antibody, and combinations thereof.

11. The kit according to claim 9, wherein the signal transduction domain is selected from the group consisting of cytoplasmic regions of CD28, CD137 (4-1BB), CD134 (OX40), DAP10 and CD27, programmed cell death-1 (PD-1), cytotoxic T-lymphocyte antigen 4 (CTLA-4), cytoplasmic regions of CD3 chains, DAP12, and activating Fc receptors.

12. The kit according to claim 9, wherein the nucleic acid comprises a nucleotide sequence according to SEQ ID NO: 1, 9, 13 or 16 encoding for a universal chimeric antigen receptor with an amino acid sequence according to SEQ ID NO: 17, 18, 19, or 20.

* * * * *

UNITED STATES PATENT AND TRADEMARK OFFICE
CERTIFICATE OF CORRECTION

| | |
|---|---|
| PATENT NO. | : 11,560,426 B2 |
| APPLICATION NO. | : 16/618881 |
| DATED | : January 24, 2023 |
| INVENTOR(S) | : Armin Ehninger |

It is certified that error appears in the above-identified patent and that said Letters Patent is hereby corrected as shown below:

In the Specification

At Column 5, Line 8, please delete "IL-8Ra" and insert --IL-8Rα-- therefor.
At Column 5, Line 8, please delete "IL-8Rp" and insert --IL-8Rβ-- therefor.
At Column 5, Line 8, please delete "IL-11Ra" and insert --IL-11Rα-- therefor.
At Column 5, Line 8, please delete "IL-11Rp" and insert --IL-11Rβ-- therefor.
At Column 5, Line 9, please delete "IL-13Ra1" and insert --IL-13Rα1-- therefor.
At Column 6, Line 37, please delete "avβ5-binding" and insert --αvβ5-binding-- therefor.
At Column 8, Line 10, please delete "PEF1a" and insert --PEF1α-- therefor.
At Column 13, Line 53, please delete "CD8a" and insert --CD8α-- therefor.

In the Claims

At Column 57, Claim 5, please delete "which contains SEQ ID NO: 25" in Formula I and insert --which contains SEQ ID NO: 28-- therefor.

Signed and Sealed this
Twenty-seventh Day of June, 2023

Katherine Kelly Vidal
*Director of the United States Patent and Trademark Office*

SEQUENCE LISTING

```
<160> NUMBER OF SEQ ID NOS: 28

<210> SEQ ID NO 1
<211> LENGTH: 1806
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Homo sapiens/Mus musculus chimera

<400> SEQUENCE: 1
atgcgccgca tgcagctgct gcttctgatc gctctgagcc tggctcttgt gaccaactct      60
gaattccagg tgcagctggt gcagagcgga gccgaggtga agaagcctgg agcctctgtg     120
aaggtgagct gcaaggcttc tggctacacc ttcacccact actacatcta ctgggtgaga     180
caggctcccg gacagggcct ggagtggatg ggaggcgtga accccagcaa cggaggcacc     240
cacttcaacg agaagttcaa gtctcgcgtg accatgaccc gcgacaccag catctctacc     300
gcttacatgg agctgagccg cctgcgctct gatgataccc tgtgtacta ctgcgctcgc     360 agcgagtacg attacggact gggcttcgcc tactggggcc agggaaccct ggtgaccgtg     420
agctctggag gcggaggcag cggaggcggc ggatctggag gcggaggaag cgatatcgtg     480
atgacccagt ctcctgatag cctggctgtg agcctggcg agagagctac catcaactgc     540
aagagcagcc agagcctgct gaactctcgc accctaaga actaccttgc ttggtaccag     600
cagaagcctg gacagccccc taagctgctg atctactggg cttctacccg caagagcggc     660
gtgcccgaca gattctctgg cagcggaagc ggcaccgatt tcaccctgac catcagcagc     720
```

```
ctgcaggctg aggacgtggc cgtgtactac tgcaagcagt cttacaacct gctgaccttc      780
ggaggcggaa ccaaggtgga gatcaaggct gccgctggag gaggcggcag caagatcctg      840
gtcaaacagt cccctatgct ggtcgcttac gacaacgccg ttaatctgag ttgcaaatat      900
agttacaacc tgtttagccg ggaatttcgc gcatctctcc acaagggact ggattctgcg      960
gttgaggttt gtgtggtcta tggcaattat agccagcaac tgcaagtgta cagcaaaaca     1020
ggctttaact gcgacgggaa actcgggaac gaatcagtga ccttctatct gcagaacctg     1080
tacgttaacc aaacagatat ttacttctgc aagatagagg tgatggctcc accgccagca     1140
ctggataaca gaagtccaa tggaaccatc attcacgtca aggggaagca tctgtgtcct      1200
tccccgttgt tccctgggcc gagcaaaccc ttttgggtgc ttgtggtagt tggcggggta     1260
ttggcctgct attcccttct cgtaactgtg gccttcatca tcttctgggt cagatctaag     1320
aggtctaggg gcgggcatag cgactacatg aacatgacac ccaggcggcc tggcccact      1380 cgcaaacact accagccata cgcaccacca agagactttg ccgcatatcg gagtggtggc     1440
ggcgggtcag gaggtggagc tagcggtgga ggaggttcct tctctaggtc agctgatgct     1500
cccgcctatc agcaaggtca gaaccagctc tacaatgagc tgaatctggg acgtcgggag     1560
gagtacgacg tgctggataa acgaagagga cgcgatcccg agatgggtgg gaagcctagg     1620
cgcaagaatc cccaggaagg cctctacaat gaactgcaga agacaagat ggccgaagcc      1680 tacagcgaga ttggcatgaa aggggagcga cggagaggaa agggacatga cgggttgtat     1740
cagggtcttt ccactgcgac aaaggatacc tatggggctc tgcacatgca agcactgcca     1800
cctaga                                                                1806

<210> SEQ ID NO 2
<211> LENGTH: 60
<212> TYPE: DNA
<213> ORGANISM: Homo sapiens

<400> SEQUENCE: 2
atgcgccgca tgcagctgct gcttctgatc gctctgagcc tggctcttgt gaccaactct        60

<210> SEQ ID NO 3
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Homo sapiens/Mus musculus chimera

<400> SEQUENCE: 3
caggtgcagc tggtgcagag cggagccgag gtgaagaagc ctggagcctc tgtgaaggtg        60
agctgcaagg cttctggcta caccttcacc cactactaca tctactgggt gagacaggct       120
cccggacagg gcctggagtg gatgggaggc gtgaacccca gcaacggagg cacccacttc       180
aacgagaagt tcaagtctcg cgtgaccatg acccgcgaca ccagcatctc taccgcttac       240
atggagctga gccgcctgcg ctctgatgat accgctgtgt actactgcgc tcgcagcgag       300
tacgattacg gactgggctt cgcctactgg ggccagggaa ccctggtgac cgtgagctct       360

<210> SEQ ID NO 4
<211> LENGTH: 336
<212> TYPE: DNA
<213> ORGANISM: Artificial Sequence
```

```
<220> FEATURE:
<223> OTHER INFORMATION: Description of Artificial Sequence: Synthetic
      polynucleotide
<220> FEATURE:
<223> OTHER INFORMATION: Homo sapiens/Mus musculus chimera

<400> SEQUENCE: 4
gatatcgtga tgacccagtc tcctgatagc ctggctgtga gcctgggcga gagagctacc    60
atcaactgca agagcagcca gagcctgctg aactctcgca cccctaagaa ctaccttgct   120
tggtaccagc agaagcctgg acagccccct aagctgctga tctactgggc ttctacccgc   180
aagagcggcg tgcccgacag attctctggc agcggaagcg gcaccgattt caccctgacc   240
atcagcagcc tgcaggctga ggacgtggcc gtgtactact gcaagcagtc ttacaacctg   300
ctgaccttcg gaggcggaac caaggtggag atcaag                              336

<210> SEQ ID NO 5
<211> LENGTH: 399
<212> TYPE: DNA
<213> ORGANISM: Homo sapiens

<400> SEQUENCE: 5
aagatcctgg tcaaacagtc ccctatgctg gtcgcttacg acaacgccgt taatctgagt    60
tgcaaatata gttacaacct gtttagccgg gaatttcgcg catctctcca caagggactg   120
gattctgcgg ttgaggtttg tgtggtctat ggcaattata ccagcaact gcaagtgtac    180 agcaaaacag gctttaactg cgacgggaaa ctcgggaacg aatcagtgac cttctatctg   240
cagaacctgt acgttaacca aacagatatt tacttctgca agatagaggt gatggctcca   300
ccgccagcac tggataacga gaagtccaat ggaaccatca ttcacgtcaa ggggaagcat   360
ctgtgtcctt ccccgttgtt ccctgggccg agcaaaccc                           399

<210> SEQ ID NO 6
<211> LENGTH: 81
<212> TYPE: DNA
<213> ORGANISM: Homo sapiens

<400> SEQUENCE: 6
ttttgggtgc ttgtggtagt tggcggggta ttggcctgct attcccttct cgtaactgtg    60
gccttcatca tcttctgggt c                                               81

<210> SEQ ID NO 7
<211> LENGTH: 123
<212> TYPE: DNA
<213> ORGANISM: Homo sapiens

<400> SEQUENCE: 7
agatctaaga ggtctagggg cgggcatagc gactacatga acatgacacc caggcggcct    60 ggcccccactc gcaaacacta ccagccatac gcaccaccaa gagactttgc cgcatatcgg   120
agt                                                                  123

<210> SEQ ID NO 8
<211> LENGTH: 327
<212> TYPE: DNA
<213> ORGANISM: Homo sapiens

<400> SEQUENCE: 8
ttctctaggt cagctgatgc tcccgcctat cagcaaggtc agaaccagct ctacaatgag    60
ctgaatctgg gacgtcggga ggagtacgac gtgctggata aacgaagagg acgcgatccc   120
```
gagatgggtg ggaagcctag gcgcaagaat ccccaggaag gcctctacaa tgaactgcag    180
aaagacaaga tggccgaagc ctacagcgag attggcatga aggggagcg acggagagga    240 aagggacatg acgggttgta tcagggtctt tccactgcga caaaggatac ctatggggct    300
ctgcacatgc aagcactgcc acctaga                                       327

<210> SEQ ID NO 9
<211> LENGTH: 1512
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Homo sapiens/Mus musculus chimera

<400> SEQUENCE: 9
atgcgccgca tgcagctgct gcttctgatc gctctgagcc tggctcttgt gaccaactct     60
gaattccagg tgcagctggt gcagagcgga gccgaggtga agaagcctgg agcctctgtg    120
aaggtgagct gcaaggcttc tggctacacc ttcacccact actacatcta ctgggtgaga    180
caggctcccg gacagggcct ggagtggatg ggaggcgtga accccagcaa cggaggcacc    240
cacttcaacg agaagttcaa gtctcgcgtg accatgaccc gcgacaccag catctctacc    300
gcttacatgg agctgagccg cctgcgctct gatgataccc tgtgtacta ctgcgctcgc    360 agcgagtacg attacggact gggcttcgcc tactgggggcc agggaaccct ggtgaccgtg    420
agctctggag gcggaggcag cggaggcggc ggatctggag gcgaggaag cgatatcgtg    480 atgacccagt ctcctgatag cctggctgtg agcctgggcg agagagctac catcaactgc    540
aagagcagcc agagcctgct gaactctcgc accctaaga actaccttgc ttggtaccag    600
cagaagcctg gacagccccc taagctgctg atctactggg cttctacccg caagagcggc    660
gtgcccgaca gattctctgg cagcggaagc ggcaccgatt tcaccctgac catcagcagc    720
ctgcaggctg aggacgtggc cgtgtactac tgcaagcagt cttacaacct gctgaccttc    780
ggaggcggaa ccaaggtgga gatcaaggga ggaggcgggt caaccactac ccctgctccc    840
aggcctccta caccccgcgcc aacgattgcc agtcaacctc tgtccctgag gcctgaagcc    900
tgcagaccag ctgcaggcgg tgctgtgcat acacgggggct tggactttgc ctgcgatatc    960
tacatctggg cacctcttgc cgggacttgt ggcgttctcc tgctttctct ggtcattacc   1020
ctgtactgtg gaggcggcgg tagcaaacgc ggacggaaga aactgctgta catcttcaag   1080
cagcccttca tgcgccccgt gcagacaaca caggaagagg acggttgcag ctgccgatt   1140 cccgaagagg aggagggagg ctgtgaattg gcggaggag gctccttctc tcgcagtgca   1200
gatgccccag cgtacaagca aggccagaac cagctgtaca acgagctcaa tctggggcgt   1260
agagaggagt atgacgtgct ggacaagagg cgaggaaggg accccgagat gggtggcaaa   1320
ccgcggcgta agaatccgca ggaaggcctc tacaacgagc tgcagaaaga caagatggcc   1380
gaagcctatt ccgagatagg gatgaaaggg gaaagacggc gcggtaaagg gcacgatggg   1440
ctctatcagg gtctgagcac tgcaaccaag gacacgtatg atgccttgca catgcaagct   1500
cttccaccaa ga                                                      1512

<210> SEQ ID NO 10
<211> LENGTH: 135
<212> TYPE: DNA
<213> ORGANISM: Homo sapiens

<400> SEQUENCE: 10

| | | |
|---|---|---|
| accactaccc ctgctcccag gcctcctaca cccgcgccaa cgattgccag tcaacctctg | 60 |
| tccctgaggc ctgaagcctg cagaccagct gcaggcggtg ctgtgcatac acggggcttg | 120 |
| gactttgcct gcgat | 135 |

<210> SEQ ID NO 11
<211> LENGTH: 72
<212> TYPE: DNA
<213> ORGANISM: Homo sapiens

<400> SEQUENCE: 11

| | | |
|---|---|---|
| atctacatct gggcacctct tgccgggact tgtggcgttc tcctgctttc tctggtcatt | 60 |
| accctgtact gt | 72 |

<210> SEQ ID NO 12
<211> LENGTH: 126
<212> TYPE: DNA
<213> ORGANISM: Homo sapiens

<400> SEQUENCE: 12

| | | |
|---|---|---|
| aaacgcggac ggaagaaact gctgtacatc ttcaagcagc ccttcatgcg ccccgtgcag | 60 |
| acaacacagg aagaggacgg ttgcagctgc cgatttcccg aagaggagga gggaggctgt | 120 |
| gaattg | 126 |

<210> SEQ ID NO 13
<211> LENGTH: 1806
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Homo sapiens/Mus musculus chimera

<400> SEQUENCE: 13

| | | |
|---|---|---|
| atgcgccgca tgcagctgct gcttctgatc gctctgagcc tggctcttgt gaccaactct | 60 |
| gaattccagg tggaggtgca actggtcgaa agtggcggtg gtttagttca gcctggtgga | 120 |
| agtctacggc ttagctgcgc agcatccggt ttcacctttta gcacttttga tgaactgg | 180 |
| gttcggcagg ctccgggcaa aggactggag tgggttgggc aaatccgcaa caaaccgaat | 240 |
| aactacgaaa cttattactc agatagcctg aagggtcgat tcaccatcag cagggatgat | 300 |
| tcaaagtcaa tcacttacct acagatgaac tcattaagag cggaggatac tgcggtgtat | 360 |
| tactgtacac taggtaactc ctggttcgcg tattggggac agggcaccct tgtaaccgtc | 420 |
| tccagcggag gcggaggcag cggaggcggc ggatctggag gcggaggaag cgacattgtt | 480 |
| atgacccaga gcccggactc tctcgctgtt agtcttggtg agcgagcgac tattaactgc | 540 |
| cggagcagtc agagtttgtt ggactctcgg acgaaaaaga actacctggc atggtaccag | 600 |
| cagaagccgg gccaaccacc taaattactg atatattggg cgtcgactcg tgagtcaggg | 660 |
| gtaccggaca ggttttctgg aagcggatca ggaacagact tcactttgac gatctcttcg | 720 |
| cttcaagccg aggacgttgc ggtttattat tgtaagcaaa gctataatct gccgacattt | 780 |
| ggtggcggca ccaaggttga aattaaggct gccgctggag gaggcggcag caagatcctg | 840 |
| gtcaaacagt cccctatgct ggtcgcttac gacaacgccg ttaatctgag ttgcaaatat | 900 |
| agttacaacc tgtttagccg ggaatttcgc gcatctctcc acaagggact ggattctgcg | 960 |

```
gttgaggttt gtgtggtcta tggcaattat agccagcaac tgcaagtgta cagcaaaaca      1020
ggctttaact gcgacgggaa actcgggaac gaatcagtga ccttctatct gcagaacctg      1080
tacgttaacc aaacagatat ttacttctgc aagatagagg tgatggctcc accgccagca      1140
ctggataacg agaagtccaa tggaaccatc attcacgtca aggggaagca tctgtgtcct      1200
tccccgttgt tccctgggcc gagcaaaccc ttttgggtgc ttgtggtagt tggcggggta      1260
ttggcctgct attcccttct cgtaactgtg gccttcatca tcttctgggt cagatctaag      1320
aggtctaggg gcgggcatag cgactacatg aacatgacac ccaggcggcc tggccccact      1380
cgcaaacact accagccata cgcaccacca agagactttg ccgcatatcg gagtggtggc      1440
ggcgggtcag gaggtggagc tagcggtgga ggaggttcct tctctaggtc agctgatgct      1500
cccgcctatc agcaaggtca gaaccagctc tacaatgagc tgaatctggg acgtcgggag      1560
gagtacgacg tgctggataa acgaagagga cgcgatcccg agatgggtgg aagcctagg      1620 cgcaagaatc cccaggaagg cctctacaat gaactgcaga agacaagat ggccgaagcc       1680 tacagcgaga ttggcatgaa aggggagcga cggagaggaa agggacatga cgggttgtat      1740
cagggtcttt ccactgcgac aaaggatacc tatggggctc tgcacatgca agcactgcca      1800
cctaga                                                                 1806
```

<210> SEQ ID NO 14
<211> LENGTH: 354
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Homo sapiens/Mus musculus chimera

<400> SEQUENCE: 14

```
gaggtgcaac tggtcgaaag tggcggtggt ttagttcagc ctggtggaag tctacggctt        60
agctgcgcag catccggttt cacctttagc gacttttgga tgaactgggt tcggcaggct      120
ccgggcaaag gactggagtg ggttgggcaa atccgcaaca aaccgaataa ctacgaaact      180
tattactcag atagcctgaa gggtcgattc accatcagca gggatgattc aaagtcaatc      240
acttacctac agatgaactc attaagagcg gaggatactg cggtgtatta ctgtacacta      300
ggtaactcct ggttcgcgta ttggggacag ggcacccttg taaccgtctc cagc            354
```

<210> SEQ ID NO 15
<211> LENGTH: 336
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Homo sapiens/Mus musculus chimera

<400> SEQUENCE: 15

```
gacattgtta tgacccagag cccggactct ctcgctgtta gtcttggtga gcgagcgact       60
attaactgcc ggagcagtca gagtttgttg gactctcgga cgaaaagaa ctacctggca      120 tggtaccagc agaagccggg ccaaccacct aaattactga tatattgggc gtcgactcgt      180
gagtcagggg taccggacag gttttctgga agcggatcag gaacagactt cactttgacg      240
atctcttcgc ttcaagccga ggacgttgcg gtttattatt gtaagcaaag ctataatctg      300
```
ccgacatttg gtggcggcac caaggttgaa attaag 336

<210> SEQ ID NO 16
<211> LENGTH: 1506
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Homo sapiens/Mus musculus chimera

<400> SEQUENCE: 16

```
atgcgccgca tgcagctgct gcttctgatc gctctgagcc tggctcttgt gaccaactct    60
gaattcgagg tgcaactggt cgaaagtggc ggtggtttag ttcagcctgg tggaagtcta   120
cggcttagct gcgcagcatc cggtttcacc tttagcgact tttggatgaa ctgggttcgg   180
caggctccgg gcaaaggact ggagtgggtt gggcaaatcc gcaacaaacc gaataactac   240
gaaacttatt actcagatag cctgaaggg cgattcacca tcagcaggga tgattcaaag   300
tcaatcactt acctacagat gaactcatta agagcggagg atactgcggt gtattactgt   360
acactaggta actcctggtt cgcgtattgg ggacagggca cccttgtaac cgtctccagc   420
ggaggcggag gcagcggagg cggcggatct ggaggcggag gaagcgacat tgttatgacc   480
cagagcccgg actctctcgc tgttagtctt ggtgagcgag cgactattaa ctgccggagc   540
agtcagagtt tgttggactc tcggacgaaa aagaactacc tggcatggta ccagcagaag   600
ccgggccaac cacctaaatt actgatatat tgggcgtcga ctcgtgagtc agggtaccg   660
gacaggtttt ctggaagcgg atcaggaaca gacttcactt tgacgatctc ttcgcttcaa   720
gccgaggacg ttgcggttta ttattgtaag caaagctata atctgccgac atttggtggc   780
ggcaccaagg ttgaaattaa gggaggaggc gggtcaacca ctaccctgc tcccaggcct   840
cctacacccg cgccaacgat tgccagtcaa cctctgtccc tgaggcctga agcctgcaga   900
ccagctgcag gcggtgctgt gcatacacgg ggcttggact ttgcctgcga tatctacatc   960
tgggcacctc ttgccgggac ttgtggcgtt ctcctgcttt ctctggtcat taccctgtac  1020
tgtggaggcg gcgtagcaa acgcggacgg aagaaactgc tgtacatctt caagcagccc  1080
ttcatgcgcc ccgtgcagac aacacaggaa gaggacggtt gcagctgccg atttcccgaa  1140
gaggaggagg aggctgtgaa attgggcgga ggaggctcct tctctcgcag tgcagatgcc  1200
ccagcgtaca gcaaggcca gaaccagctg tacaacgagc tcaatctggg gcgtagagag  1260
gagtatgacg tgctggacaa gaggcgagga agggaccccg agatgggtgg caaaccgcgg  1320
cgtaagaatc cgcaggaagg cctctacaac gagctgcaga agacaagat ggccgaagcc  1380
tattccgaga tagggatgaa aggggaaaga cggcgcggta agggcacga tgggctctat  1440
cagggtctga gcactgcaac caaggacacg tatgatgcct tgcacatgca agctcttcca  1500
ccaaga                                                              1506
```

<210> SEQ ID NO 17
<211> LENGTH: 602
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Homo sapiens/Mus musculus chimera

<400> SEQUENCE: 17

```
Met Arg Arg Met Gln Leu Leu Leu Ile Ala Leu Ser Leu Ala Leu
1               5                   10                  15

Val Thr Asn Ser Glu Phe Gln Val Gln Leu Val Gln Ser Gly Ala Glu
                20                  25                  30

Val Lys Lys Pro Gly Ala Ser Val Lys Val Ser Cys Lys Ala Ser Gly
            35                  40                  45

Tyr Thr Phe Thr His Tyr Tyr Ile Tyr Trp Val Arg Gln Ala Pro Gly
        50                  55                  60

Gln Gly Leu Glu Trp Met Gly Gly Val Asn Pro Ser Asn Gly Gly Thr
65              70                  75                  80

His Phe Asn Glu Lys Phe Lys Ser Arg Val Thr Met Thr Arg Asp Thr
                85                  90                  95

Ser Ile Ser Thr Ala Tyr Met Glu Leu Ser Arg Leu Arg Ser Asp Asp
            100                 105                 110

Thr Ala Val Tyr Tyr Cys Ala Arg Ser Glu Tyr Asp Tyr Gly Leu Gly
        115                 120                 125

Phe Ala Tyr Trp Gly Gln Gly Thr Leu Val Thr Val Ser Ser Gly Gly
    130                 135                 140

Gly Gly Ser Gly Gly Gly Gly Ser Gly Gly Gly Gly Ser Asp Ile Val
145             150                 155                 160

Met Thr Gln Ser Pro Asp Ser Leu Ala Val Ser Leu Gly Glu Arg Ala
                165                 170                 175

Thr Ile Asn Cys Lys Ser Ser Gln Ser Leu Leu Asn Ser Arg Thr Pro
            180                 185                 190

Lys Asn Tyr Leu Ala Trp Tyr Gln Gln Lys Pro Gly Gln Pro Pro Lys
        195                 200                 205

Leu Leu Ile Tyr Trp Ala Ser Thr Arg Lys Ser Gly Val Pro Asp Arg
    210                 215                 220

Phe Ser Gly Ser Gly Ser Gly Thr Asp Phe Thr Leu Thr Ile Ser Ser
225             230                 235                 240

Leu Gln Ala Glu Asp Val Ala Val Tyr Tyr Cys Lys Gln Ser Tyr Asn
                245                 250                 255

Leu Leu Thr Phe Gly Gly Gly Thr Lys Val Glu Ile Lys Ala Ala Ala
            260                 265                 270

Gly Gly Gly Gly Ser Lys Ile Leu Val Lys Gln Ser Pro Met Leu Val
        275                 280                 285

Ala Tyr Asp Asn Ala Val Asn Leu Ser Cys Lys Tyr Ser Tyr Asn Leu
    290                 295                 300

Phe Ser Arg Glu Phe Arg Ala Ser Leu His Lys Gly Leu Asp Ser Ala
305             310                 315                 320

Val Glu Val Cys Val Val Tyr Gly Asn Tyr Ser Gln Gln Leu Gln Val
                325                 330                 335

Tyr Ser Lys Thr Gly Phe Asn Cys Asp Gly Lys Leu Gly Asn Glu Ser
            340                 345                 350

Val Thr Phe Tyr Leu Gln Asn Leu Tyr Val Asn Gln Thr Asp Ile Tyr
        355                 360                 365

Phe Cys Lys Ile Glu Val Met Ala Pro Pro Ala Leu Asp Asn Glu
    370                 375                 380

Lys Ser Asn Gly Thr Ile Ile His Val Lys Gly Lys His Leu Cys Pro
385             390                 395                 400

Ser Pro Leu Phe Pro Gly Pro Ser Lys Pro Phe Trp Val Leu Val Val
            405                 410                 415
```

-continued

```
Val Gly Gly Val Leu Ala Cys Tyr Ser Leu Leu Val Thr Val Ala Phe
            420                 425                 430

Ile Ile Phe Trp Val Arg Ser Lys Arg Ser Arg Gly Gly His Ser Asp
        435                 440                 445

Tyr Met Asn Met Thr Pro Arg Arg Pro Gly Pro Thr Arg Lys His Tyr
    450                 455                 460

Gln Pro Tyr Ala Pro Pro Arg Asp Phe Ala Ala Tyr Arg Ser Gly Gly
465                 470                 475                 480

Gly Gly Ser Gly Gly Gly Ala Ser Gly Gly Gly Ser Phe Ser Arg
                485                 490                 495

Ser Ala Asp Ala Pro Ala Tyr Gln Gln Gly Gln Asn Gln Leu Tyr Asn
            500                 505                 510

Glu Leu Asn Leu Gly Arg Arg Glu Glu Tyr Asp Val Leu Asp Lys Arg
        515                 520                 525

Arg Gly Arg Asp Pro Glu Met Gly Gly Lys Pro Arg Arg Lys Asn Pro
    530                 535                 540

Gln Glu Gly Leu Tyr Asn Glu Leu Gln Lys Asp Lys Met Ala Glu Ala
545                 550                 555                 560

Tyr Ser Glu Ile Gly Met Lys Gly Glu Arg Arg Arg Gly Lys Gly His
                565                 570                 575

Asp Gly Leu Tyr Gln Gly Leu Ser Thr Ala Thr Lys Asp Thr Tyr Gly
            580                 585                 590

Ala Leu His Met Gln Ala Leu Pro Pro Arg
        595                 600

<210> SEQ ID NO 18
<211> LENGTH: 504
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Homo sapiens/Mus musculus chimera

<400> SEQUENCE: 18

Met Arg Arg Met Gln Leu Leu Leu Ile Ala Leu Ser Leu Ala Leu
1               5                   10                  15

Val Thr Asn Ser Glu Phe Gln Val Gln Leu Val Gln Ser Gly Ala Glu
            20                  25                  30

Val Lys Lys Pro Gly Ala Ser Val Lys Val Ser Cys Lys Ala Ser Gly
        35                  40                  45

Tyr Thr Phe Thr His Tyr Ile Tyr Trp Val Arg Gln Ala Pro Gly
    50                  55                  60

Gln Gly Leu Glu Trp Met Gly Val Asn Pro Ser Asn Gly Gly Thr
65                  70                  75                  80

His Phe Asn Glu Lys Phe Lys Ser Arg Val Thr Met Thr Arg Asp Thr
                85                  90                  95

Ser Ile Ser Thr Ala Tyr Met Glu Leu Ser Arg Leu Arg Ser Asp Asp
            100                 105                 110

Thr Ala Val Tyr Tyr Cys Ala Arg Ser Glu Tyr Asp Tyr Gly Leu Gly
        115                 120                 125

Phe Ala Tyr Trp Gly Gln Gly Thr Leu Val Thr Val Ser Ser Gly Gly
    130                 135                 140

Gly Gly Ser Gly Gly Gly Gly Ser Gly Gly Gly Gly Ser Asp Ile Val
145                 150                 155                 160
```

```
Met Thr Gln Ser Pro Asp Ser Leu Ala Val Ser Leu Gly Glu Arg Ala
            165                 170                 175

Thr Ile Asn Cys Lys Ser Ser Gln Ser Leu Leu Asn Ser Arg Thr Pro
        180                 185                 190

Lys Asn Tyr Leu Ala Trp Tyr Gln Gln Lys Pro Gly Gln Pro Pro Lys
    195                 200                 205

Leu Leu Ile Tyr Trp Ala Ser Thr Arg Lys Ser Gly Val Pro Asp Arg
210                 215                 220

Phe Ser Gly Ser Gly Ser Gly Thr Asp Phe Thr Leu Thr Ile Ser Ser
225                 230                 235                 240

Leu Gln Ala Glu Asp Val Ala Val Tyr Tyr Cys Lys Gln Ser Tyr Asn
                245                 250                 255

Leu Leu Thr Phe Gly Gly Gly Thr Lys Val Glu Ile Lys Gly Gly Gly
            260                 265                 270

Gly Ser Thr Thr Thr Pro Ala Pro Arg Pro Pro Thr Pro Ala Pro Thr
        275                 280                 285

Ile Ala Ser Gln Pro Leu Ser Leu Arg Pro Glu Ala Cys Arg Pro Ala
    290                 295                 300

Ala Gly Gly Ala Val His Thr Arg Gly Leu Asp Phe Ala Cys Asp Ile
305                 310                 315                 320

Tyr Ile Trp Ala Pro Leu Ala Gly Thr Cys Gly Val Leu Leu Leu Ser
                325                 330                 335

Leu Val Ile Thr Leu Tyr Cys Gly Gly Gly Ser Lys Arg Gly Arg
            340                 345                 350

Lys Lys Leu Leu Tyr Ile Phe Lys Gln Pro Phe Met Arg Pro Val Gln
            355                 360                 365

Thr Thr Gln Glu Glu Asp Gly Cys Ser Cys Arg Phe Pro Glu Glu Glu
        370                 375                 380

Glu Gly Gly Cys Glu Leu Gly Gly Gly Ser Phe Ser Arg Ser Ala
385                 390                 395                 400

Asp Ala Pro Ala Tyr Lys Gln Gly Gln Asn Gln Leu Tyr Asn Glu Leu
                405                 410                 415

Asn Leu Gly Arg Arg Glu Glu Tyr Asp Val Leu Asp Lys Arg Arg Gly
            420                 425                 430

Arg Asp Pro Glu Met Gly Gly Lys Pro Arg Arg Lys Asn Pro Gln Glu
        435                 440                 445

Gly Leu Tyr Asn Glu Leu Gln Lys Asp Lys Met Ala Glu Ala Tyr Ser
    450                 455                 460

Glu Ile Gly Met Lys Gly Glu Arg Arg Arg Gly Lys Gly His Asp Gly
465                 470                 475                 480

Leu Tyr Gln Gly Leu Ser Thr Ala Thr Lys Asp Thr Tyr Asp Ala Leu
                485                 490                 495

His Met Gln Ala Leu Pro Pro Arg
            500

<210> SEQ ID NO 19
<211> LENGTH: 602
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Homo sapiens/Mus musculus chimera

<400> SEQUENCE: 19
```

```
Met Arg Arg Met Gln Leu Leu Leu Leu Ile Ala Leu Ser Leu Ala Leu
1               5                   10                  15
Val Thr Asn Ser Glu Phe Gln Val Glu Val Gln Leu Val Glu Ser Gly
            20                  25                  30
Gly Gly Leu Val Gln Pro Gly Gly Ser Leu Arg Leu Ser Cys Ala Ala
            35                  40                  45
Ser Gly Phe Thr Phe Ser Asp Phe Trp Met Asn Trp Val Arg Gln Ala
        50                  55                  60
Pro Gly Lys Gly Leu Glu Trp Val Gly Gln Ile Arg Asn Lys Pro Asn
65                  70                  75                  80
Asn Tyr Glu Thr Tyr Tyr Ser Asp Ser Leu Lys Gly Arg Phe Thr Ile
                85                  90                  95
Ser Arg Asp Asp Ser Lys Ser Ile Thr Tyr Leu Gln Met Asn Ser Leu
            100                 105                 110
Arg Ala Glu Asp Thr Ala Val Tyr Tyr Cys Thr Leu Gly Asn Ser Trp
            115                 120                 125
Phe Ala Tyr Trp Gly Gln Gly Thr Leu Val Thr Val Ser Ser Gly Gly
        130                 135                 140
Gly Gly Ser Gly Gly Gly Ser Gly Gly Gly Ser Asp Ile Val
145                 150                 155                 160
Met Thr Gln Ser Pro Asp Ser Leu Ala Val Ser Leu Gly Glu Arg Ala
            165                 170                 175
Thr Ile Asn Cys Arg Ser Ser Gln Ser Leu Leu Asp Ser Arg Thr Lys
            180                 185                 190
Lys Asn Tyr Leu Ala Trp Tyr Gln Gln Lys Pro Gly Gln Pro Pro Lys
        195                 200                 205
Leu Leu Ile Tyr Trp Ala Ser Thr Arg Glu Ser Gly Val Pro Asp Arg
210                 215                 220
Phe Ser Gly Ser Gly Ser Gly Thr Asp Phe Thr Leu Thr Ile Ser Ser
225                 230                 235                 240
Leu Gln Ala Glu Asp Val Ala Val Tyr Tyr Cys Lys Gln Ser Tyr Asn
            245                 250                 255
Leu Pro Thr Phe Gly Gly Gly Thr Lys Val Glu Ile Lys Ala Ala Ala
            260                 265                 270
Gly Gly Gly Gly Ser Lys Ile Leu Val Lys Gln Ser Pro Met Leu Val
        275                 280                 285
Ala Tyr Asp Asn Ala Val Asn Leu Ser Cys Lys Tyr Ser Tyr Asn Leu
        290                 295                 300
Phe Ser Arg Glu Phe Arg Ala Ser Leu His Lys Gly Leu Asp Ser Ala
305                 310                 315                 320
Val Glu Val Cys Val Val Tyr Gly Asn Tyr Ser Gln Gln Leu Gln Val
            325                 330                 335
Tyr Ser Lys Thr Gly Phe Asn Cys Asp Gly Lys Leu Gly Asn Glu Ser
            340                 345                 350
Val Thr Phe Tyr Leu Gln Asn Leu Tyr Val Asn Gln Thr Asp Ile Tyr
        355                 360                 365
Phe Cys Lys Ile Glu Val Met Ala Pro Pro Ala Leu Asp Asn Glu
        370                 375                 380
Lys Ser Asn Gly Thr Ile Ile His Val Lys Gly Lys His Leu Cys Pro
385                 390                 395                 400
Ser Pro Leu Phe Pro Gly Pro Ser Lys Pro Phe Trp Val Leu Val Val
            405                 410                 415
Val Gly Gly Val Leu Ala Cys Tyr Ser Leu Leu Val Thr Val Ala Phe
```

```
                420             425             430
Ile Ile Phe Trp Val Arg Ser Lys Arg Ser Arg Gly Gly His Ser Asp
            435             440             445

Tyr Met Asn Met Thr Pro Arg Arg Pro Gly Pro Thr Arg Lys His Tyr
            450             455             460

Gln Pro Tyr Ala Pro Pro Arg Asp Phe Ala Ala Tyr Arg Ser Gly Gly
465             470             475             480

Gly Gly Ser Gly Gly Gly Ala Ser Gly Gly Gly Ser Phe Ser Arg
            485             490             495

Ser Ala Asp Ala Pro Ala Tyr Gln Gln Gly Gln Asn Gln Leu Tyr Asn
            500             505             510

Glu Leu Asn Leu Gly Arg Arg Glu Glu Tyr Asp Val Leu Asp Lys Arg
            515             520             525

Arg Gly Arg Asp Pro Glu Met Gly Gly Lys Pro Arg Arg Lys Asn Pro
            530             535             540

Gln Glu Gly Leu Tyr Asn Glu Leu Gln Lys Asp Lys Met Ala Glu Ala
545             550             555             560

Tyr Ser Glu Ile Gly Met Lys Gly Glu Arg Arg Arg Gly Lys Gly His
            565             570             575

Asp Gly Leu Tyr Gln Gly Leu Ser Thr Ala Thr Lys Asp Thr Tyr Gly
            580             585             590

Ala Leu His Met Gln Ala Leu Pro Pro Arg
            595             600

<210> SEQ ID NO 20
<211> LENGTH: 502
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Homo sapiens/Mus musculus chimera

<400> SEQUENCE: 20

Met Arg Arg Met Gln Leu Leu Leu Ile Ala Leu Ser Leu Ala Leu
1               5                   10                  15

Val Thr Asn Ser Glu Phe Glu Val Gln Leu Val Glu Ser Gly Gly Gly
            20              25                  30

Leu Val Gln Pro Gly Gly Ser Leu Arg Leu Ser Cys Ala Ala Ser Gly
            35              40                  45

Phe Thr Phe Ser Asp Phe Trp Met Asn Trp Val Arg Gln Ala Pro Gly
        50              55                  60

Lys Gly Leu Glu Trp Val Gly Gln Ile Arg Asn Lys Pro Asn Asn Tyr
65              70              75                  80

Glu Thr Tyr Tyr Ser Asp Ser Leu Lys Gly Arg Phe Thr Ile Ser Arg
            85              90                  95

Asp Asp Ser Lys Ser Ile Thr Tyr Leu Gln Met Asn Ser Leu Arg Ala
            100             105                 110

Glu Asp Thr Ala Val Tyr Tyr Cys Thr Leu Gly Asn Ser Trp Phe Ala
            115             120                 125

Tyr Trp Gly Gln Gly Thr Leu Val Thr Val Ser Ser Gly Gly Gly Gly
            130             135                 140

Ser Gly Gly Gly Gly Ser Gly Gly Gly Gly Ser Asp Ile Val Met Thr
145             150             155                 160

Gln Ser Pro Asp Ser Leu Ala Val Ser Leu Gly Glu Arg Ala Thr Ile
```

```
            165                 170                 175
Asn Cys Arg Ser Ser Gln Ser Leu Leu Asp Ser Arg Thr Lys Lys Asn
            180                 185                 190

Tyr Leu Ala Trp Tyr Gln Gln Lys Pro Gly Gln Pro Pro Lys Leu Leu
        195                 200                 205

Ile Tyr Trp Ala Ser Thr Arg Glu Ser Gly Val Pro Asp Arg Phe Ser
    210                 215                 220

Gly Ser Gly Ser Gly Thr Asp Phe Thr Leu Thr Ile Ser Ser Leu Gln
225                 230                 235                 240

Ala Glu Asp Val Ala Val Tyr Tyr Cys Lys Gln Ser Tyr Asn Leu Pro
                245                 250                 255

Thr Phe Gly Gly Gly Thr Lys Val Glu Ile Lys Gly Gly Gly Gly Ser
            260                 265                 270

Thr Thr Thr Pro Ala Pro Arg Pro Pro Thr Pro Ala Pro Thr Ile Ala
        275                 280                 285

Ser Gln Pro Leu Ser Leu Arg Pro Glu Ala Cys Arg Pro Ala Ala Gly
    290                 295                 300

Gly Ala Val His Thr Arg Gly Leu Asp Phe Ala Cys Asp Ile Tyr Ile
305                 310                 315                 320

Trp Ala Pro Leu Ala Gly Thr Cys Gly Val Leu Leu Leu Ser Leu Val
                325                 330                 335

Ile Thr Leu Tyr Cys Gly Gly Gly Ser Lys Arg Gly Arg Lys Lys
            340                 345                 350

Leu Leu Tyr Ile Phe Lys Gln Pro Phe Met Arg Pro Val Gln Thr Thr
        355                 360                 365

Gln Glu Glu Asp Gly Cys Ser Cys Arg Phe Pro Glu Glu Glu Glu Gly
    370                 375                 380

Gly Cys Glu Leu Gly Gly Gly Ser Phe Ser Arg Ser Ala Asp Ala
385                 390                 395                 400

Pro Ala Tyr Lys Gln Gly Gln Asn Gln Leu Tyr Asn Glu Leu Asn Leu
                405                 410                 415

Gly Arg Arg Glu Glu Tyr Asp Val Leu Asp Lys Arg Gly Arg Asp
            420                 425                 430

Pro Glu Met Gly Gly Lys Pro Arg Arg Lys Asn Pro Gln Glu Gly Leu
        435                 440                 445

Tyr Asn Glu Leu Gln Lys Asp Lys Met Ala Glu Ala Tyr Ser Glu Ile
    450                 455                 460

Gly Met Lys Gly Glu Arg Arg Arg Gly Lys Gly His Asp Gly Leu Tyr
465                 470                 475                 480

Gln Gly Leu Ser Thr Ala Thr Lys Asp Thr Tyr Asp Ala Leu His Met
                485                 490                 495

Gln Ala Leu Pro Pro Arg
            500

<210> SEQ ID NO 21
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Homo sapiens/Mus musculus chimera

<400> SEQUENCE: 21

Gln Val Gln Leu Val Gln Ser Gly Ala Glu Val Lys Lys Pro Gly Ala
```

```
                 1               5                  10                  15
Ser Val Lys Val Ser Cys Lys Ala Ser Gly Tyr Thr Phe Thr His Tyr
                        20                  25                  30

Tyr Ile Tyr Trp Val Arg Gln Ala Pro Gly Gln Gly Leu Glu Trp Met
                35                  40                  45

Gly Val Asn Pro Ser Asn Gly Gly Thr His Phe Asn Glu Lys Phe
    50                  55                  60

Lys Ser Arg Val Thr Met Thr Arg Asp Thr Ser Ile Ser Thr Ala Tyr
65                  70                  75                  80

Met Glu Leu Ser Arg Leu Arg Ser Asp Thr Ala Val Tyr Tyr Cys
                    85                  90                  95

Ala Arg Ser Glu Tyr Asp Tyr Gly Leu Gly Phe Ala Tyr Trp Gly Gln
                100                 105                 110

Gly Thr Leu Val Thr Val Ser Ser
                115                 120

<210> SEQ ID NO 22
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Homo sapiens/Mus musculus chimera

<400> SEQUENCE: 22

Asp Ile Val Met Thr Gln Ser Pro Asp Ser Leu Ala Val Ser Leu Gly
1               5                  10                  15

Glu Arg Ala Thr Ile Asn Cys Lys Ser Ser Gln Ser Leu Leu Asn Ser
                20                  25                  30

Arg Thr Pro Lys Asn Tyr Leu Ala Trp Tyr Gln Gln Lys Pro Gly Gln
            35                  40                  45

Pro Pro Lys Leu Leu Ile Tyr Trp Ala Ser Thr Arg Lys Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Asn Leu Leu Thr Phe Gly Gly Gly Thr Lys Val Glu Ile Lys
                100                 105                 110

<210> SEQ ID NO 23
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Homo sapiens/Mus musculus chimera

<400> SEQUENCE: 23

Glu Val Gln Leu Val Glu Ser Gly Gly Gly Leu Val Gln Pro Gly Gly
1               5                  10                  15

Ser Leu Arg Leu Ser Cys Ala Ala Ser Gly Phe Thr Phe Ser Asp Phe
                20                  25                  30

Trp Met Asn Trp Val Arg Gln Ala Pro Gly Lys Gly Leu Glu Trp Val
            35                  40                  45
```

Gly Gln Ile Arg Asn Lys Pro Asn Asn Tyr Glu Thr Tyr Tyr Ser Asp
        50                  55                  60

Ser Leu Lys Gly Arg Phe Thr Ile Ser Arg Asp Asp Ser Lys Ser Ile
 65                  70                  75                  80

Thr Tyr Leu Gln Met Asn Ser Leu Arg Ala Glu Asp Thr Ala Val Tyr
                 85                  90                  95

Tyr Cys Thr Leu Gly Asn Ser Trp Phe Ala Tyr Trp Gly Gln Gly Thr
            100                 105                 110

Leu Val Thr Val Ser Ser
        115

<210> SEQ ID NO 24
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Homo sapiens/Mus musculus chimera

<400> SEQUENCE: 24

Asp Ile Val Met Thr Gln Ser Pro Asp Ser Leu Ala Val Ser Leu Gly
 1               5                  10                  15

Glu Arg Ala Thr Ile Asn Cys Arg Ser Ser Gln Ser Leu Leu Asp Ser
                 20                  25                  30

Arg Thr Lys Lys Asn Tyr Leu Ala Trp Tyr Gln Gln Lys Pro Gly Gln
             35                  40                  45

Pro Pro Lys Leu Leu Ile Tyr Trp Ala Ser Thr Arg Glu Ser Gly Val
         50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Lys Gln
                 85                  90                  95

Ser Tyr Asn Leu Pro Thr Phe Gly Gly Gly Thr Lys Val Glu Ile Lys
            100                 105                 110

<210> SEQ ID NO 25
<211> LENGTH: 10
<212> TYPE: PRT
<213> ORGANISM: Homo sapiens

<400> SEQUENCE: 25

Lys Pro Leu Pro Glu Val Thr Asp Glu Tyr
 1               5                  10

<210> SEQ ID NO 26
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Synthetic Homo sapiens sequence

<400> SEQUENCE: 26

Cys Gly Glu Met Gly Trp Val Arg Cys Gly Gly Gly Ser Gly Gly
 1               5                  10                  15

Gly Gly Ser Lys Pro Leu Pro Glu Val Thr Asp Glu Tyr Gly Gly Gly
             20                  25                  30

```
Gly Ser Gly Gly Gly Gly Ser Cys Gly Glu Met Gly Trp Val Arg Cys
        35                  40                  45

<210> SEQ ID NO 27
<211> LENGTH: 18
<212> TYPE: PRT
<213> ORGANISM: Homo sapiens

<400> SEQUENCE: 27

Glu Lys Glu Ala Leu Lys Lys Ile Ile Glu Asp Gln Gln Glu Ser Leu
1               5                   10                  15

Asn Lys

<210> SEQ ID NO 28
<211> LENGTH: 11
<212> TYPE: PRT
<213> ORGANISM: Homo sapiens

<400> SEQUENCE: 28

Ser Lys Pro Leu Pro Glu Val Thr Asp Glu Tyr
1               5                   10
```